US012350076B2

(12) United States Patent
Wong et al.

(10) Patent No.: US 12,350,076 B2
(45) Date of Patent: Jul. 8, 2025

(54) INTEGRATED COMPUTED TOMOGRAPHY (CT) TREATMENT COUCH SYSTEM

(71) Applicant: The Johns Hopkins University, Baltimore, MD (US)

(72) Inventors: John Wai-Chiu Wong, Towson, MD (US); Jeffrey H. Siewerdsen, Baltimore, MD (US); Junghoon Lee, Woodstock, MD (US)

(73) Assignee: The Johns Hopkins University, Baltimore, MD (US)

( * ) Notice: Subject to any disclaimer, the term of this patent is extended or adjusted under 35 U.S.C. 154(b) by 813 days.

(21) Appl. No.: 17/135,691

(22) Filed: Dec. 28, 2020

(65) Prior Publication Data

US 2021/0113164 A1    Apr. 22, 2021

Related U.S. Application Data

(63) Continuation-in-part of application No. PCT/US2019/039963, filed on Jun. 28, 2019, and a
(Continued)

(51) Int. Cl.
*A61B 6/04*       (2006.01)
*A61B 6/00*       (2006.01)
(Continued)

(52) U.S. Cl.
CPC ............ *A61B 6/0487* (2020.08); *A61B 6/027* (2013.01); *A61B 6/032* (2013.01); *A61B 6/0407* (2013.01);
(Continued)

(58) Field of Classification Search
None
See application file for complete search history.

(56) References Cited

U.S. PATENT DOCUMENTS

2002/0065461 A1    5/2002   Cosman
2007/0003010 A1*   1/2007   Guertin ............... A61B 6/4441
                                                              378/63
(Continued)

FOREIGN PATENT DOCUMENTS

CN      204684463 U      10/2015
CN      105079986 A      11/2015
(Continued)

OTHER PUBLICATIONS

Supplementary European Search Report for Application No. EP19825248.8, mailed on Jul. 28, 2021, 7 pages.
(Continued)

*Primary Examiner* — Katherine L Fernandez
(74) *Attorney, Agent, or Firm* — Harrity & Harrity, LLP

(57) ABSTRACT

An integrated computed tomography (CT) treatment couch system may include a base platform configured to couple to a rotatable floor component associated with a medical accelerator, a pedestal component mounted to the base platform, a treatment couchtop disposed on the pedestal component, and a CT scanner device. The CT scanner device may include a support structure and a CT gantry. The support structure may be mounted to the base platform or to the pedestal component. The CT gantry may have a bore and may be oriented such that the bore is in line with the treatment couchtop. The CT gantry may be configured to generate on-line helical CT scans to guide radiotherapy provided by the medical accelerator.

20 Claims, 17 Drawing Sheets

Related U.S. Application Data continuation-in-part of application No. PCT/US2019/039968, filed on Jun. 28, 2019.

(60) Provisional application No. 62/793,196, filed on Jan. 16, 2019, provisional application No. 62/692,441, filed on Jun. 29, 2018.

(51) Int. Cl.
    *A61B 6/02*     (2006.01)
    *A61B 6/03*     (2006.01)
    *A61B 6/50*     (2024.01)

(52) U.S. Cl.
    CPC ............ *A61B 6/4447* (2013.01); *A61B 6/504* (2013.01); *A61B 6/541* (2013.01); *A61B 6/547* (2013.01)

(56) References Cited

U.S. PATENT DOCUMENTS

| | | |
|---|---|---|
| 2007/0003021 A1 | 1/2007 | Guertin et al. |
| 2007/0153969 A1 | 7/2007 | Maschke |
| 2010/0172468 A1 | 7/2010 | Gregerson |
| 2010/0287703 A1* | 11/2010 | Zapata ................. A61B 6/5276 5/607 |
| 2012/0330087 A1* | 12/2012 | Gregerson ........... A61B 6/4447 324/309 |
| 2014/0046212 A1 | 2/2014 | Deutschmann |
| 2017/0189724 A1* | 7/2017 | Liu ....................... A61N 5/1081 |
| 2017/0340902 A1 | 11/2017 | Vilsmeier et al. |

FOREIGN PATENT DOCUMENTS

| | | |
|---|---|---|
| WO | 2011041412 A2 | 4/2011 |
| WO | 2018044726 A1 | 3/2018 |
| WO | 2018055001 A1 | 3/2018 |

OTHER PUBLICATIONS

PCT International Search Report and Written Opinion corresponding to PCT/US2019/039963, mailed Oct. 18, 2019, 13 pages.

PCT International Search Report and Written Opinion corresponding to PCT/US2019/039968, mailed Oct. 23, 2019, 14 pages.

* cited by examiner

400 →

410 — Monitor, by an integrated computed tomography (CT) treatment couch system, position information relating to the integrated CT treatment couch system and/or relating to a patient utilizing the integrated CT treatment couch system, the integrated CT treatment couch system including a base platform, a pedestal component mounted to the base platform, a treatment couchtop disposed on the pedestal component, a CT scanner device, the CT scanner device including a support structure and a CT gantry, the support structure being coupled to the base platform or to the pedestal component, the CT gantry having a bore, and being oriented such that the bore is in line with the treatment couchtop, the CT gantry being configured to provide image guidance for radiotherapy, and one or more sensors configured to generate the position information 420 — Control, by the integrated CT treatment couch system, movement of the treatment couchtop based on the position information

FIG. 4

INTEGRATED COMPUTED TOMOGRAPHY (CT) TREATMENT COUCH SYSTEM

RELATED APPLICATIONS

This application is a continuation-in-part of International Application No. PCT/US2019/039963, filed on Jun. 28, 2019, which claims priority to U.S. Provisional Patent Application No. 62/692,441, filed on Jun. 29, 2018, all contents of which are incorporated by reference herein in their entireties. This application is also a continuation-in-part of International Application No. PCT/US2019/039968, filed on Jun. 28, 2019, which claims priority to U.S. Provisional Application No. 62/793,196, filed on Jan. 16, 2019, all contents of which are incorporated by reference herein in their entireties.

BACKGROUND

A computed tomography (CT) scan involves the use of X-rays to generate cross-sectional or volumetric images of a patient's body. Radiation therapy (RT) is a cancer treatment technique that utilizes high intensity energy beams, such as X-rays, protons, or other types of particles, to target cancer cells, and is typically performed in an operating room where a patient is positioned on a treatment couch. RT typically refers to external beam RT, where the treatment beam is generated by a linear accelerator (linac) equipped with a treatment couch and an on-board imaging system (e.g., most commonly cone beam computed tomography (CBCT)) for patient positioning and treatment beam delivery.

SUMMARY

According to some implementations, an integrated computed tomography (CT) treatment couch system, may include a base platform configured to couple to a rotatable floor component associated with a medical accelerator, a pedestal component mounted to the base platform, a treatment couchtop disposed on the pedestal component, and a CT scanner device. The CT scanner device may include a support structure and a CT gantry, and the CT gantry may include a bore and be oriented such that the bore is in line with the treatment couchtop. The CT gantry may be configured to generate on-line CT scans to guide radiotherapy provided by the medical accelerator. The support structure may be mounted to the base platform or to the pedestal component, in which axial, helical, and/or volumetric CT scans of a patient on the treatment couchtop are obtained via translational motion of the treatment couchtop along an axis passing through the bore of the CT gantry, or may be configured to traverse a guided pathway coupled to, or incorporated on, the base platform, in which volumetric CT scans are obtained via translational motion of the treatment couchtop along the axis without translational motion of the CT gantry along the axis, translational motion of the CT gantry via the guided pathway along the axis without translational motion of the treatment couchtop along the axis, or combined translational motion of the treatment couchtop along the axis and the CT gantry via the guided pathway along the axis.

According to some implementations, a method may include monitoring, by an integrated computed tomography (CT) treatment couch system, position information relating to the integrated CT treatment couch system and/or relating to a patient utilizing the integrated CT treatment couch system. The integrated CT treatment couch system may include a rotatable base platform, a pedestal component mounted to the base platform, a treatment couchtop disposed on the pedestal component, and a CT scanner device. The CT scanner device may include a support structure and a CT gantry. The support structure may be coupled to the base platform or to the pedestal component. The CT gantry may have a bore and may be oriented such that the bore is in line with the treatment couchtop. The CT gantry may be configured to provide image guidance for radiotherapy. The integrated CT treatment couch system may include one or more sensors configured to generate the position information. The method may include controlling, by the integrated CT treatment couch system, movement of the treatment couchtop based on the position information.

According to some implementations, a computed tomography (CT) scanner device may be provided for an integrated computed tomography (CT) treatment couch system that includes a base platform configured to couple to a rotatable floor component associated with a medical accelerator, a pedestal component mounted to the base platform, and a treatment couchtop disposed on the pedestal component. The CT scanner device may include a support structure, and a CT gantry. The CT gantry may include a bore and may be oriented such that the bore is in line with the treatment couchtop. The CT gantry may be configured to generate on-line CT scans to guide radiotherapy provided by the medical accelerator. The support structure may be mounted to the base platform or to the pedestal component, in which axial, helical, and/or volumetric CT scans of a patient on the treatment couchtop are obtained via translational motion of the treatment couchtop along an axis passing through the bore of the CT gantry, or may be configured to traverse a guided pathway coupled to, or incorporated on, the base platform, in which volumetric CT scans are obtained via translational motion of the treatment couchtop along the axis without translational motion of the CT gantry along the axis, translational motion of the CT gantry via the guided pathway along the axis without translational motion of the treatment couchtop along the axis, or combined translational motion of the treatment couchtop along the axis and the CT gantry via the guided pathway along the axis.

BRIEF DESCRIPTION OF THE DRAWINGS

FIG. 4 is a flow chart of an example process for controlling an integrated CT treatment couch system.

DETAILED DESCRIPTION

Figure 1A:
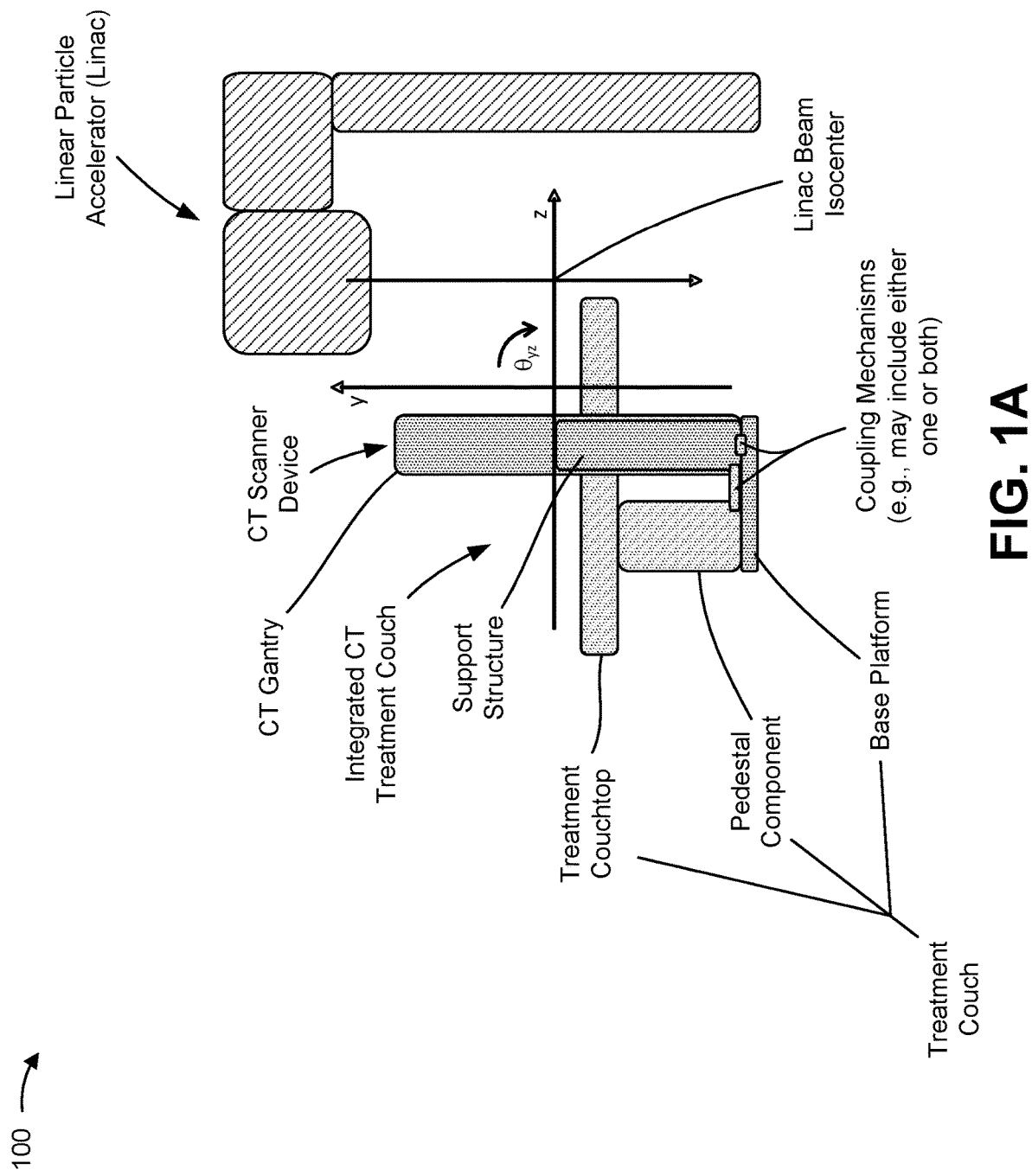
FIGS. 1A-1N are diagrams of an example implementation described herein.

The following detailed description of example implementations refers to the accompanying drawings. The same reference numbers in different drawings may identify the same or similar elements.

Currently, many radiation-based treatment configurations utilize cone beam computed tomography (CBCT) technology, in which divergent X-rays and a detector (e.g., a flat panel detector) are used to image a patient's body, for image guidance. However, there are several disadvantages with this technology. For example, a CBCT device equipped in a radiation-based treatment system, such as a linac, is limited to only about 1 rotation per minute (RPM). Incorporated in a ring configuration, a CBCT device also only has a scan rate of about 12 seconds per volume. Additionally, the quality of CBCT imaging is generally degraded due to cone-based geometry acquisition, low signal-to-noise ratio (e.g., in a typical amorphous silicon (a-Si)-based flat panel detector), susceptibility to high levels of x-ray scatter, and susceptibility to artifacts resulting from patient movements during scanning at slow speeds.

Some implementations, described herein, provide an integrated CT treatment couch system in which a CT scanner device—e.g., having a CT gantry—is included as an integral part of a treatment couch (e.g., a treatment table and/or the like) coupled to the rotatable floor platform. In some implementations, the CT gantry may include a bore, may be oriented such that the bore is in line with a treatment couchtop, and may include one or more X-ray sources (e.g., X-ray tubes) and one or more detectors (e.g., single-slice axial CT detectors, multi-detector CT (MDCT) detectors, etc.) that rotate within the CT gantry for generating axial or helical CT scans (e.g., online CT scans that are optimized for image-guided radiotherapy (IGRT)). Such scans can be acquired in either axial or helical CT acquisition modes based on translational movement of the patient setup on the treatment couchtop through the bore of the CT gantry while the CT gantry is rotating. In some implementations, the CT scanner device may include a support structure that is coupled to a pedestal component on which the treatment couchtop is supported and/or to a base platform to which the pedestal component is mounted, which allows the translation of the couchtop or the CT scanner device or a combination of both. In some implementations, the base platform may be configured for coupling to a rotatable floor component that is centered to a beam isocenter axis of a medical accelerator. In some implementations, rotation of the rotatable floor component may cause both the CT scanner device and the treatment couchtop to kick (e.g., rotate) about the beam isocenter axis.

In this way, online CT scans (axial or helical CT scans) for IGRT and/or treatment planning may be obtained, in a treatment room, via CT scanner capabilities provided onboard a treatment couch. Integrating a CT scanner device that can provide axial or helical CT scans, rather than CBCT-based scans (as are commonly used in the treatment room in current systems), yields higher quality CT scans, permits a variety of potential CT acquisition modes (e.g., dual-energy CT), and permits faster CT scan speeds. Additionally, providing an integrated CT scanner device on a treatment couch system also reduces or eliminates a need to include, or utilize, a CBCT-based scanner on a treatment gantry of a linac, reduces or eliminates a need for such a CBCT-based scanner to be folded away during treatment (as is required if non-coplanar treatments involving rotated treatment couch "kick" with or without oblique beam arrangements), and/or allows the use of a smaller imaging panel for the purpose of kilovoltage (kV) radiographic or fluoroscopic imaging. This conserves costs, improves the IGRT process, shortens treatment times, and increases overall patient throughput. Furthermore, integrating the CT scanner device and the treatment couchtop (e.g., which may simply replace an existing treatment couch), such that both the CT scanner device and the treatment couchtop are rotatable (e.g., as an integrated unit) about a beam isocenter axis of a typical linac, also permits non-coplanar treatments with a "couch kick," as described above, without requiring any overhaul, or costly changes, to be made to the linac (this is, for example, in contrast to recently-proposed advanced treatment machines, which all sacrifice the non-coplanar capabilities by eliminating couch rotation capabilities in favor of improved imaging). Moreover, utilizing an integrated CT scanner device also reduces or eliminates a need to arrange for, and utilize, a typical standalone CT scanning system for IGRT purposes. For example, use of a standalone CT scanner configuration, such as one in which the CT gantry is movable on rails (e.g., a CT-on-rails system in the treatment room), would involve additional patient motion in the treatment room (e.g., including turning a conventional treatment couch toward the CT gantry for CT scanning, and then turning the conventional treatment couch back in line with the linac for patient treatment). This involves manual effort and additional time—e.g., time during which the patient may move (e.g., including internal organ motion and/or the like), which may affect the treatment procedure. In contrast, having an integrated CT scanner device that remains in line with the treatment couchtop and the patient, even when the treatment couchtop is moved (e.g., with a couch kick), as described herein, simplifies switching between CT scanning and patient treatment in the treatment room, which shortens treatment times and increases overall patient throughput.

Figure 1B:
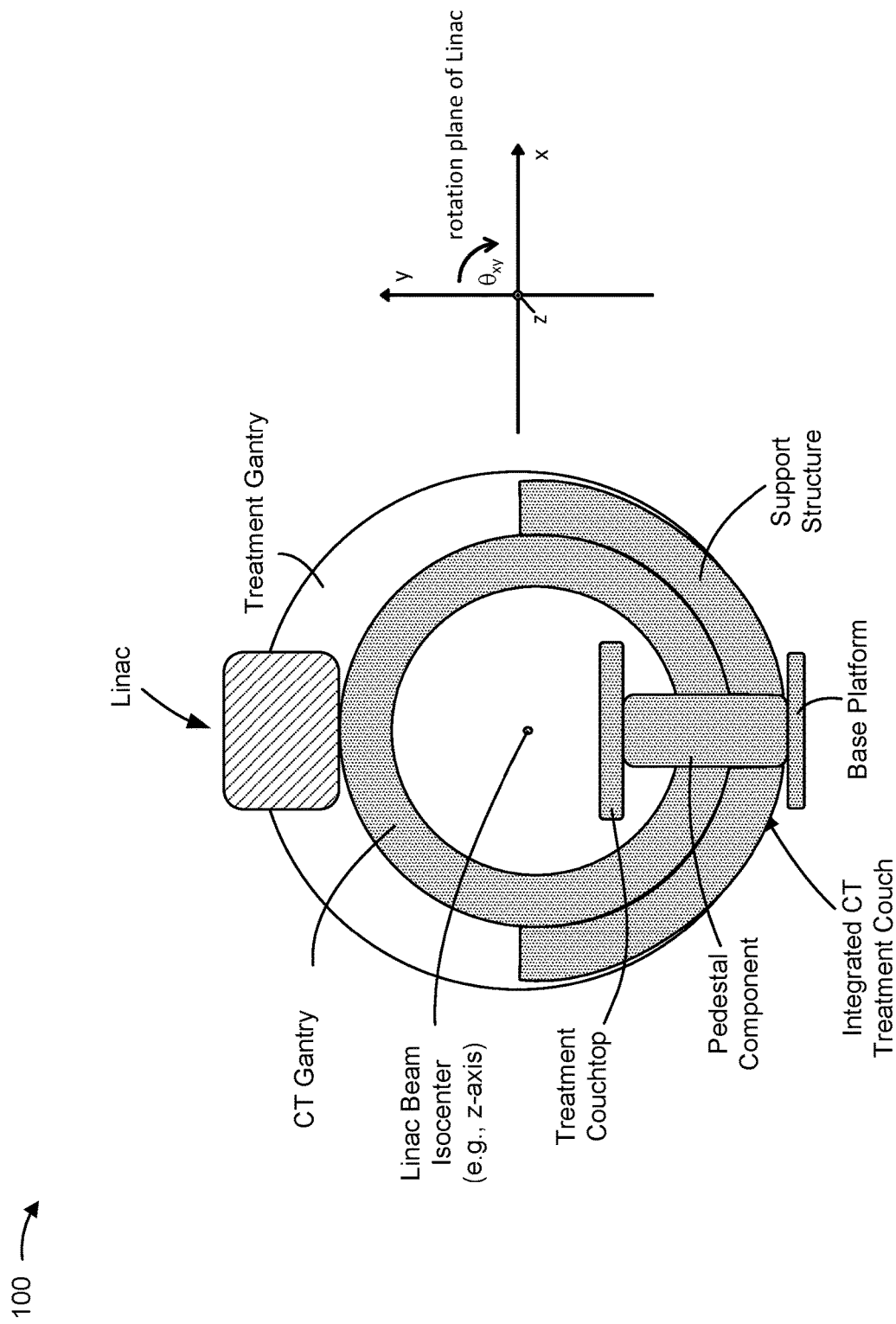
Figure 1C:
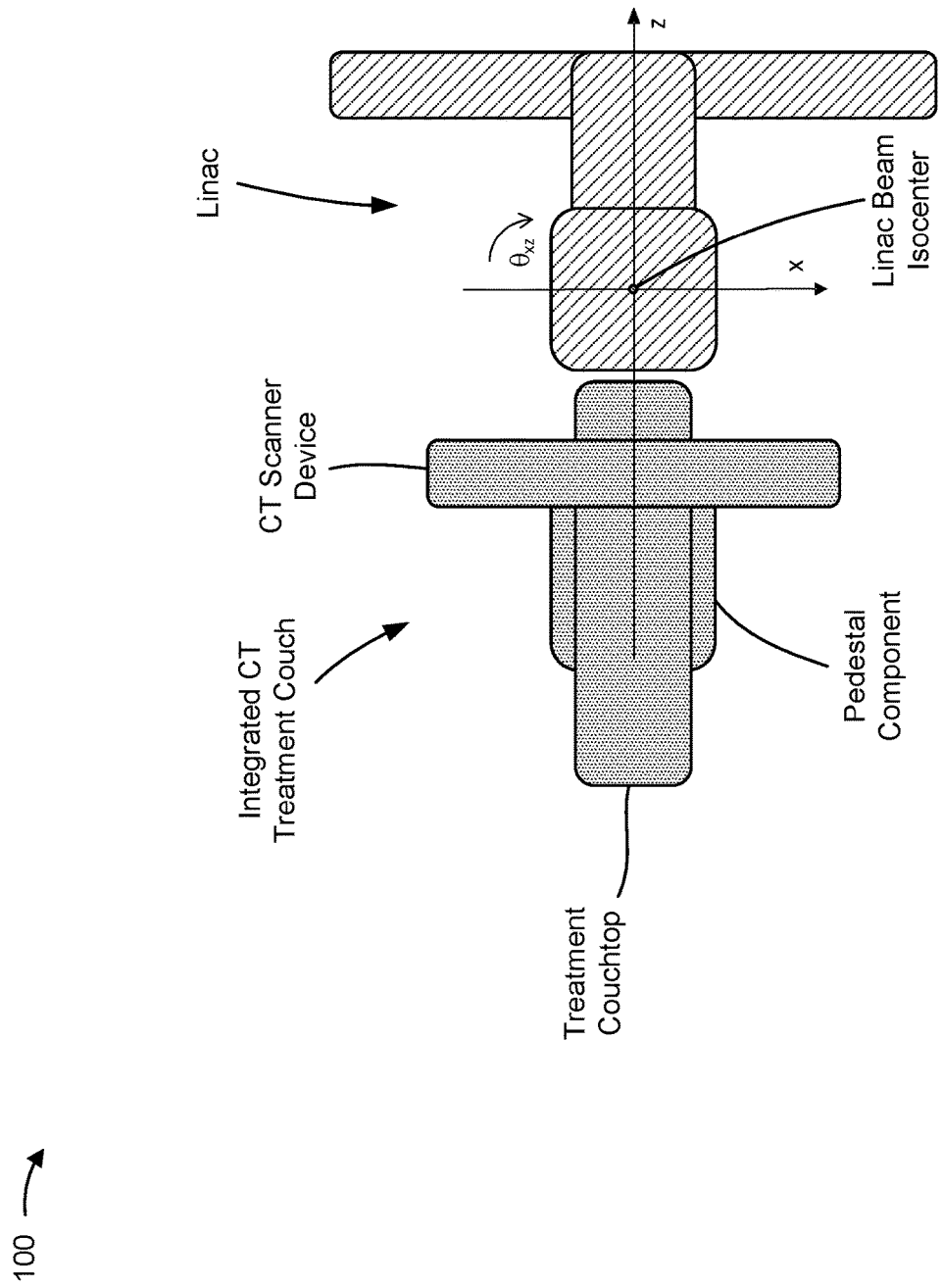
Figure 1D:
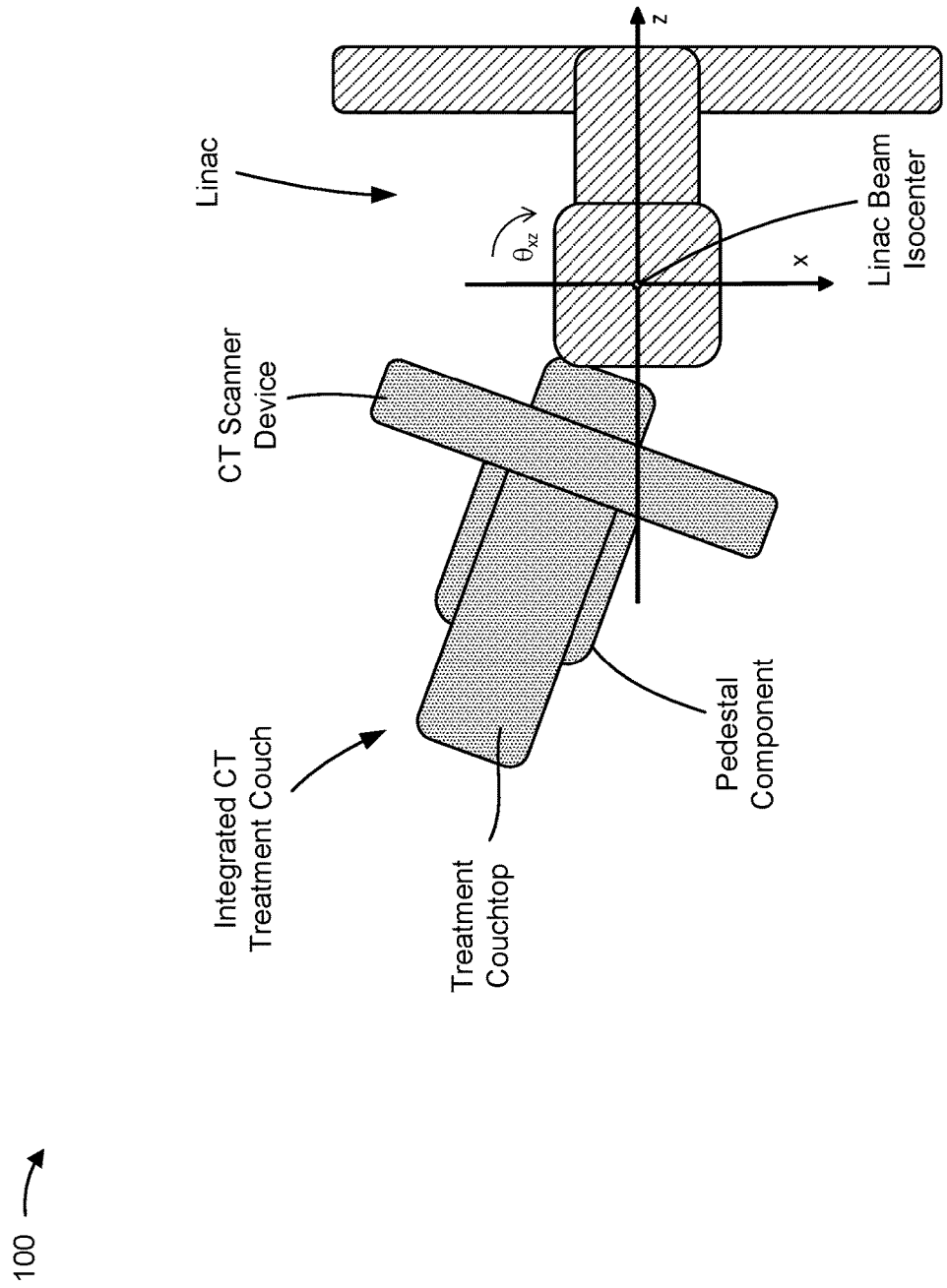
Figure 1E:
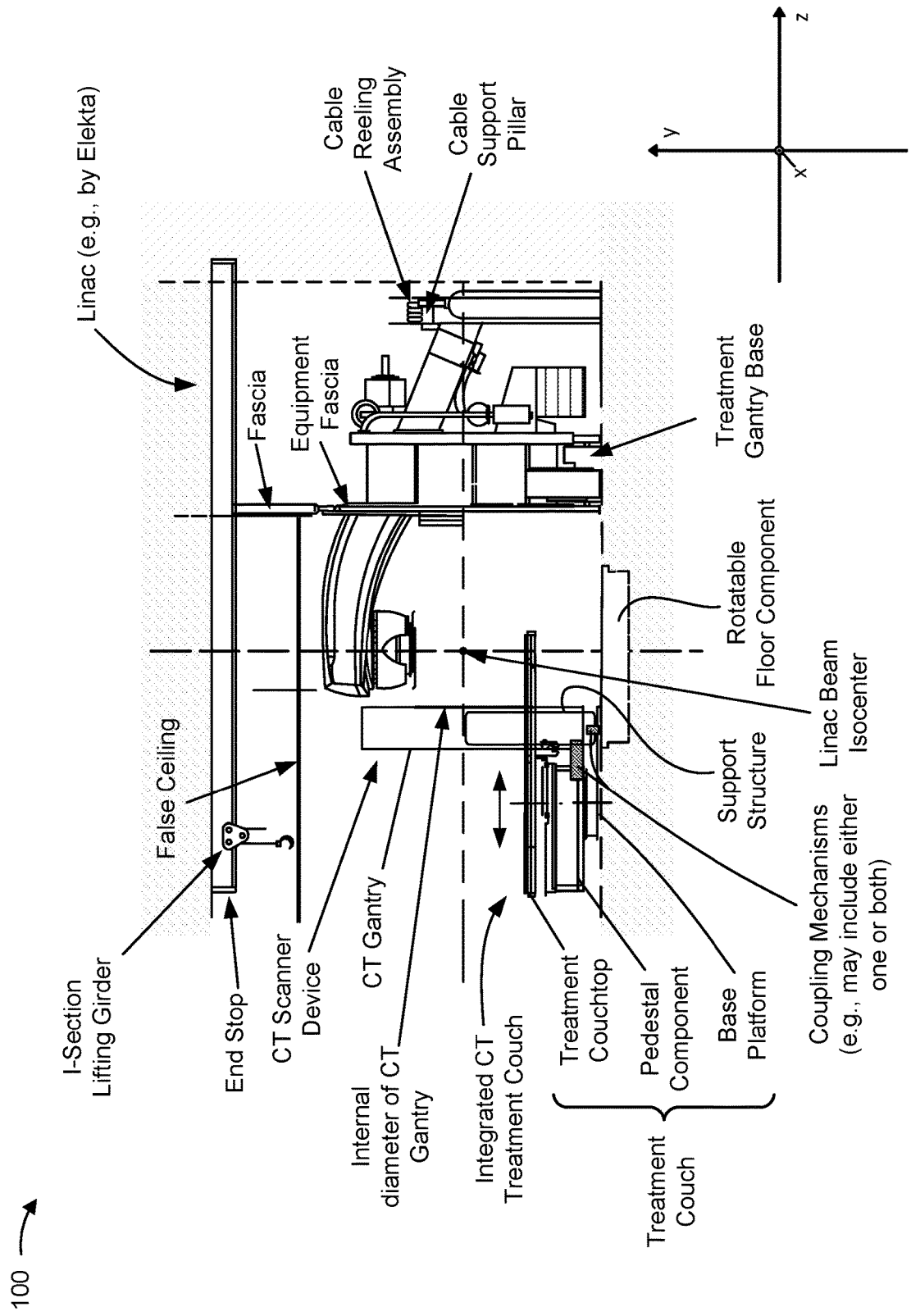
Figure 1F:
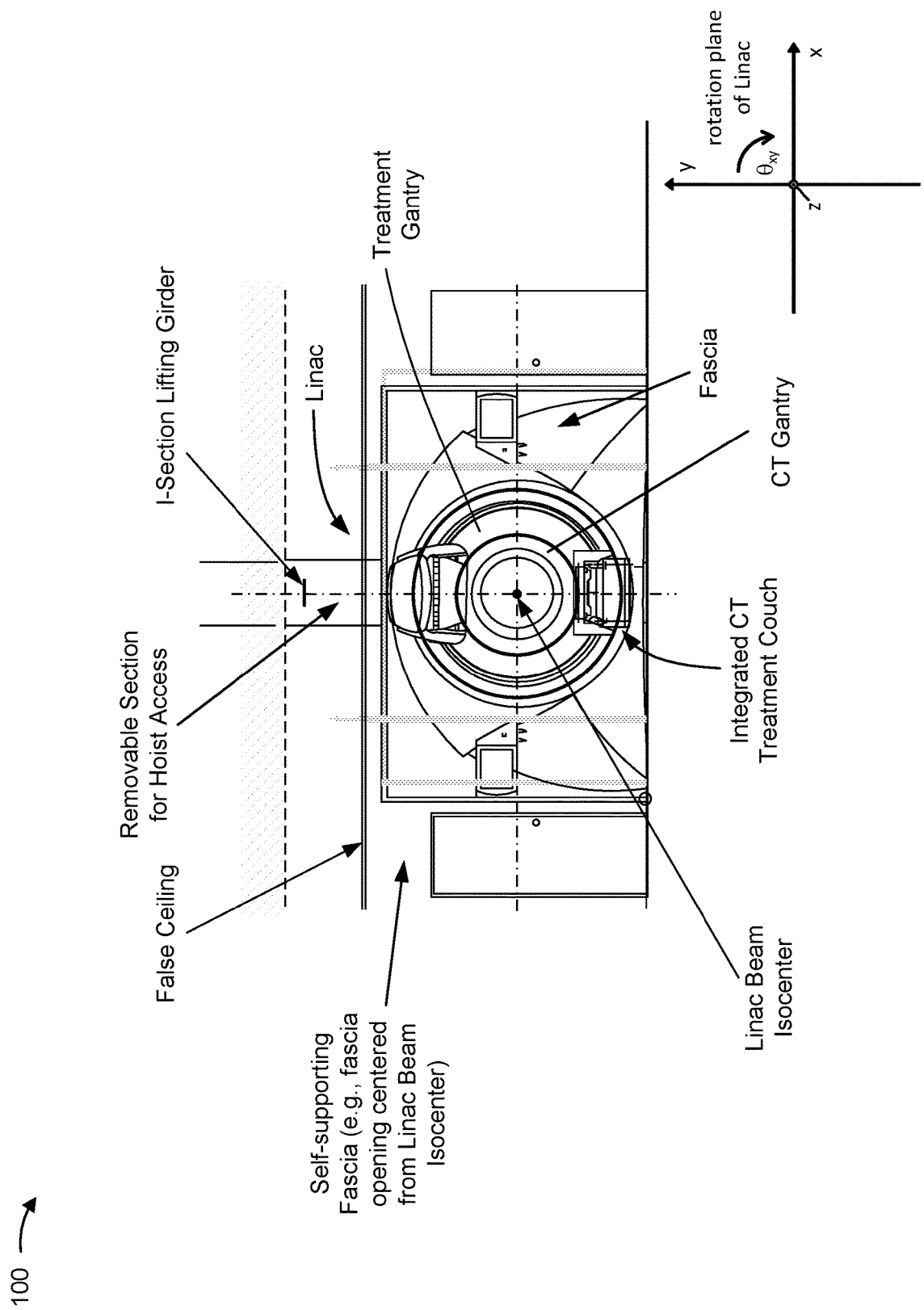
Figure 1G:
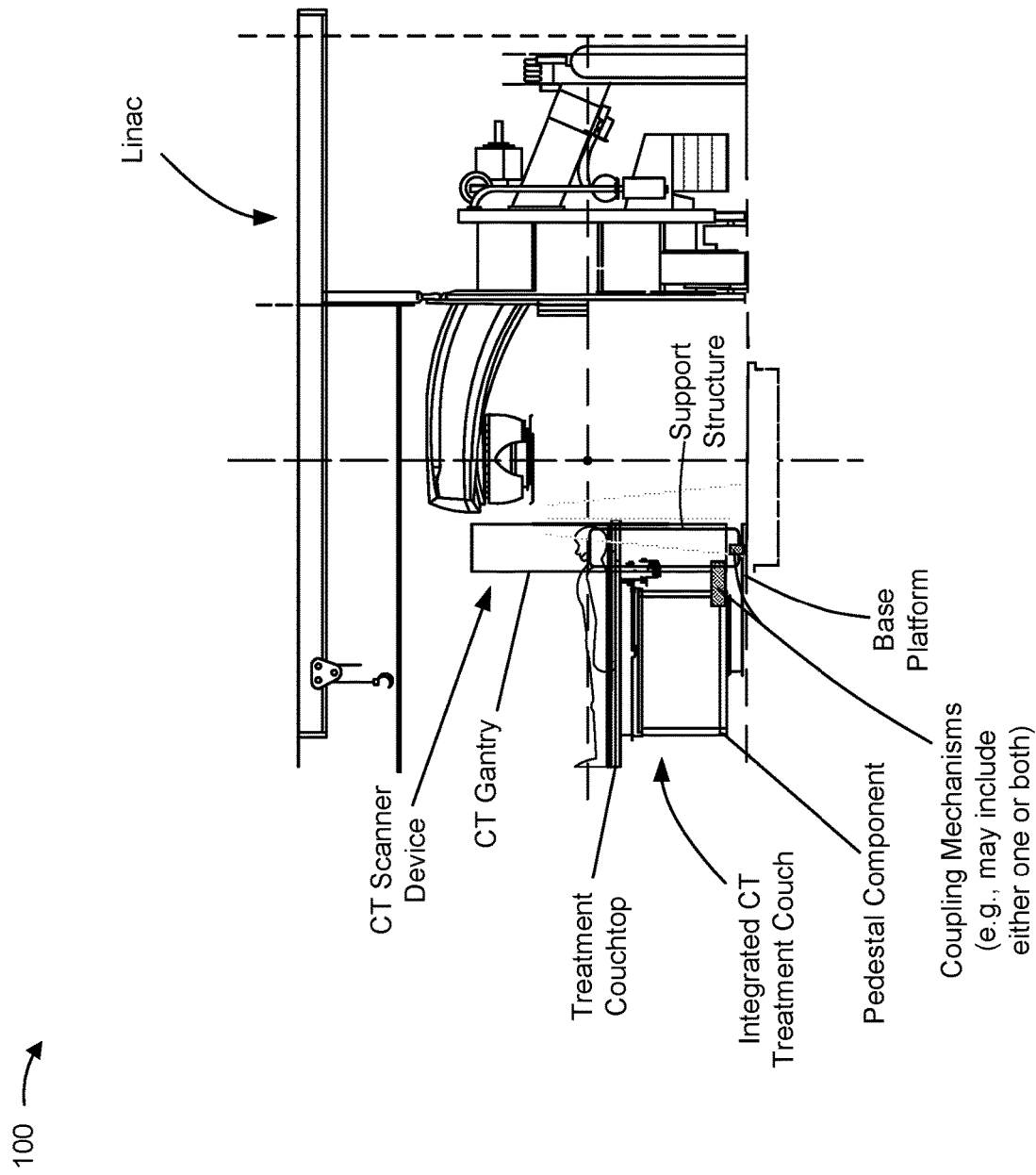
Figure 1H:
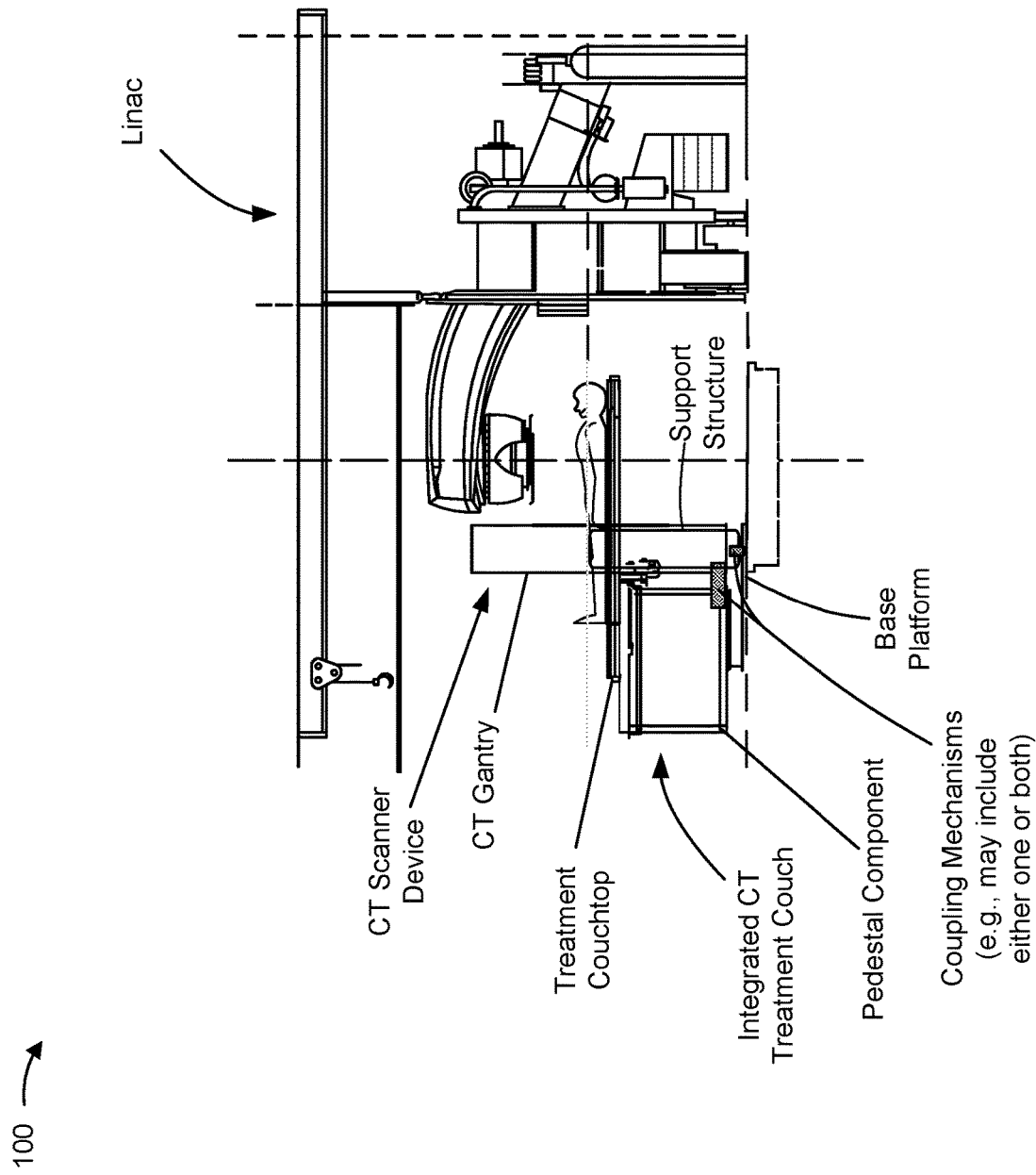
Figure 1I:
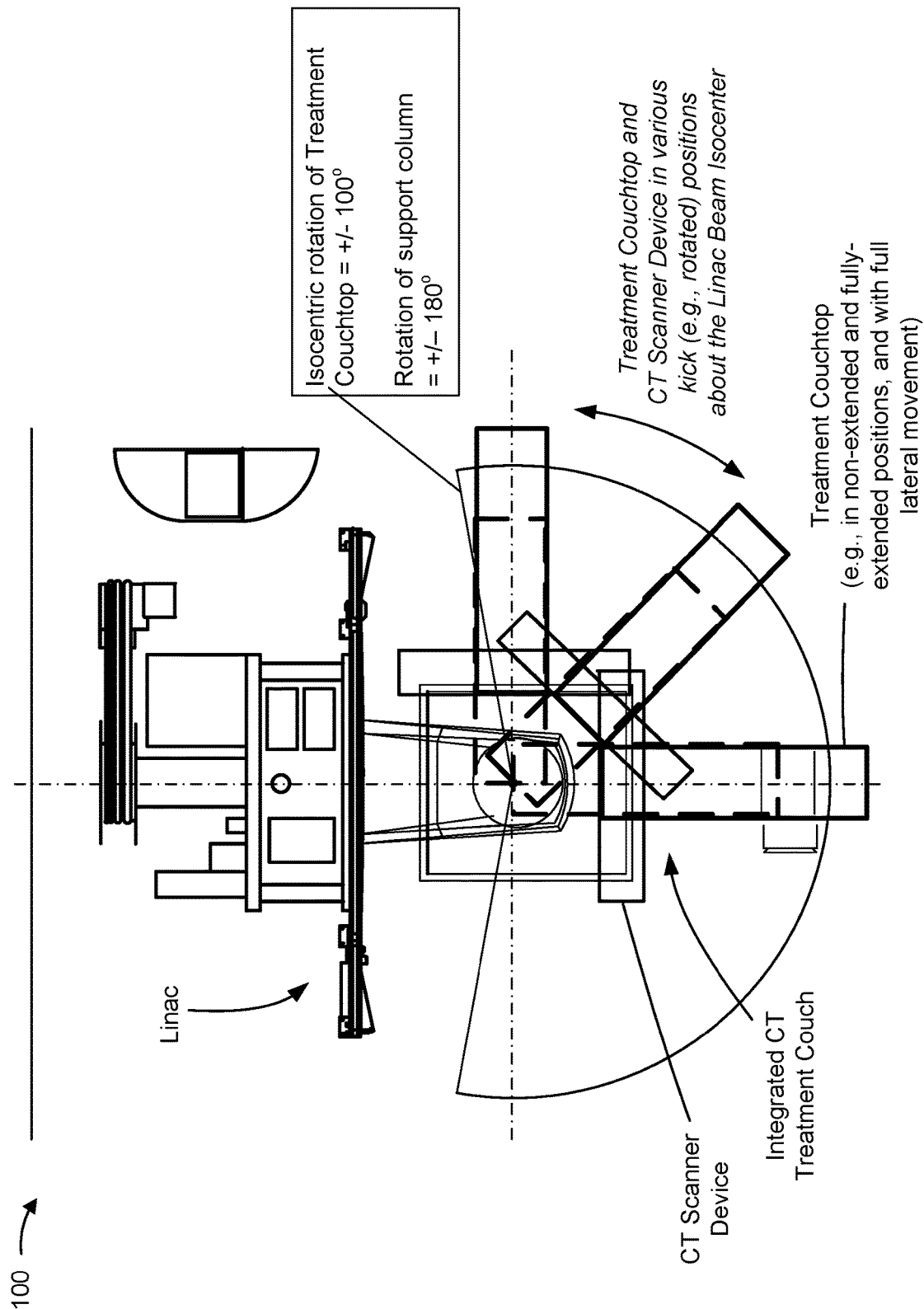
Figure 1J:
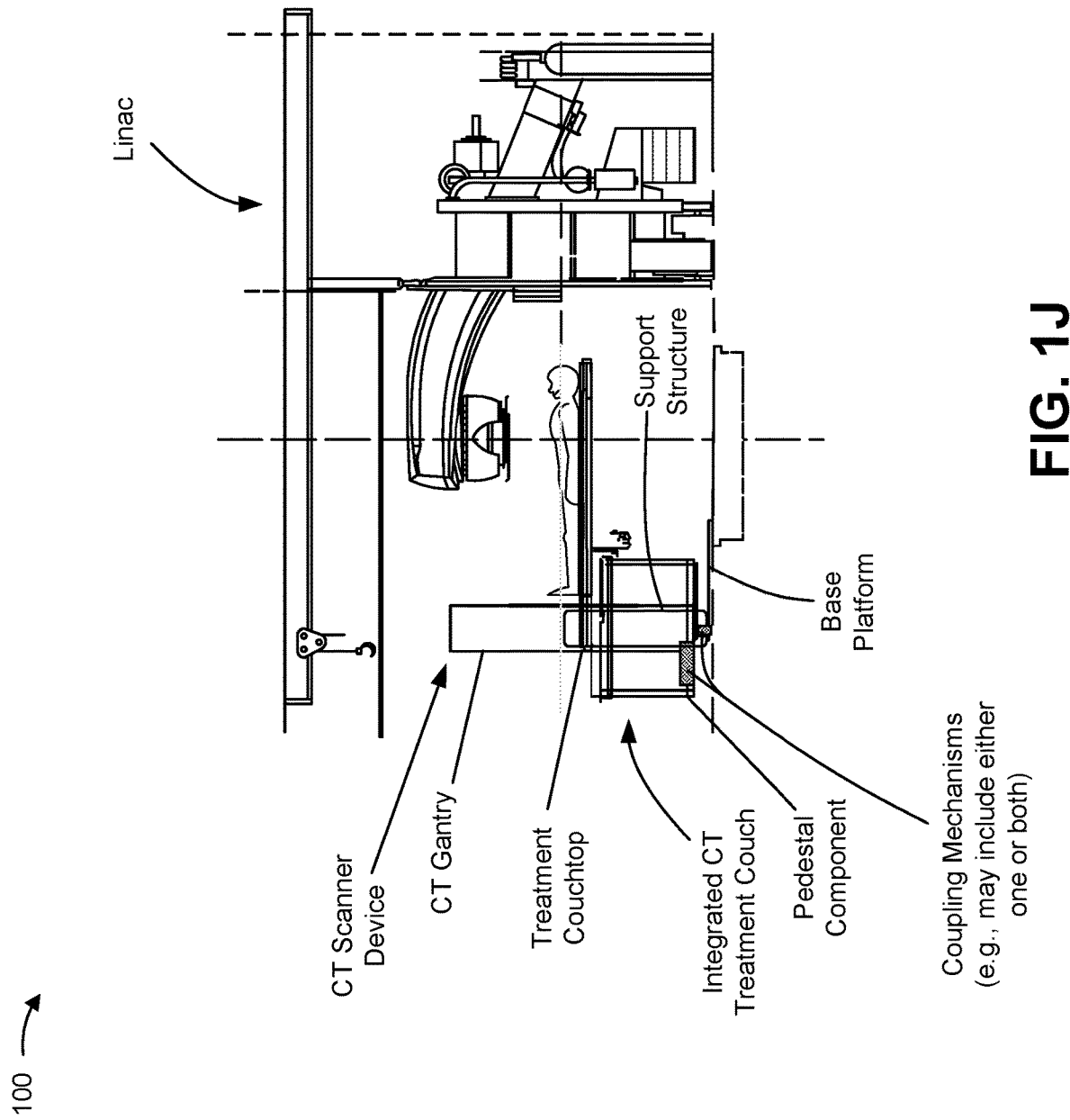
Figure 1K:
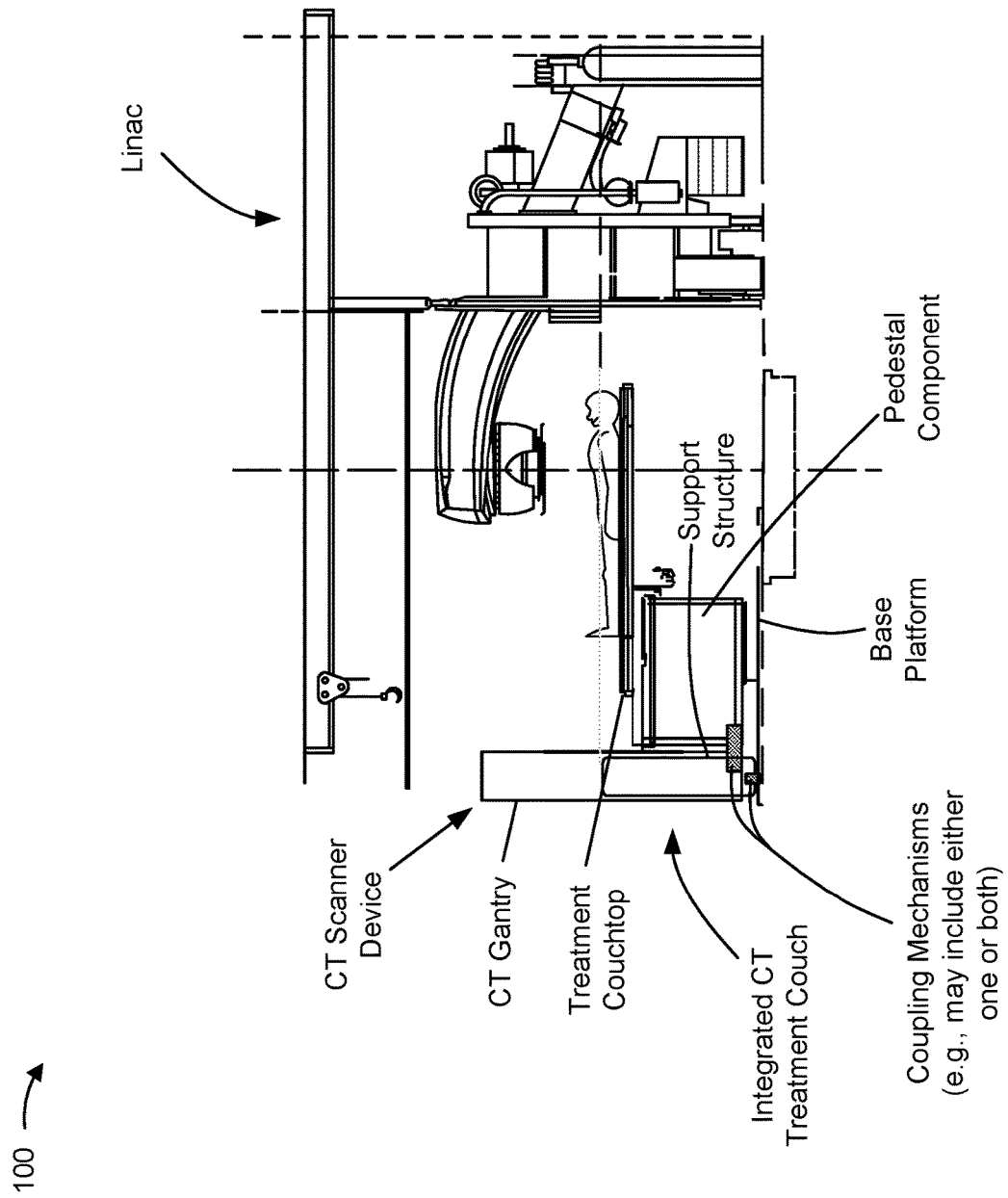
Figure 1L:
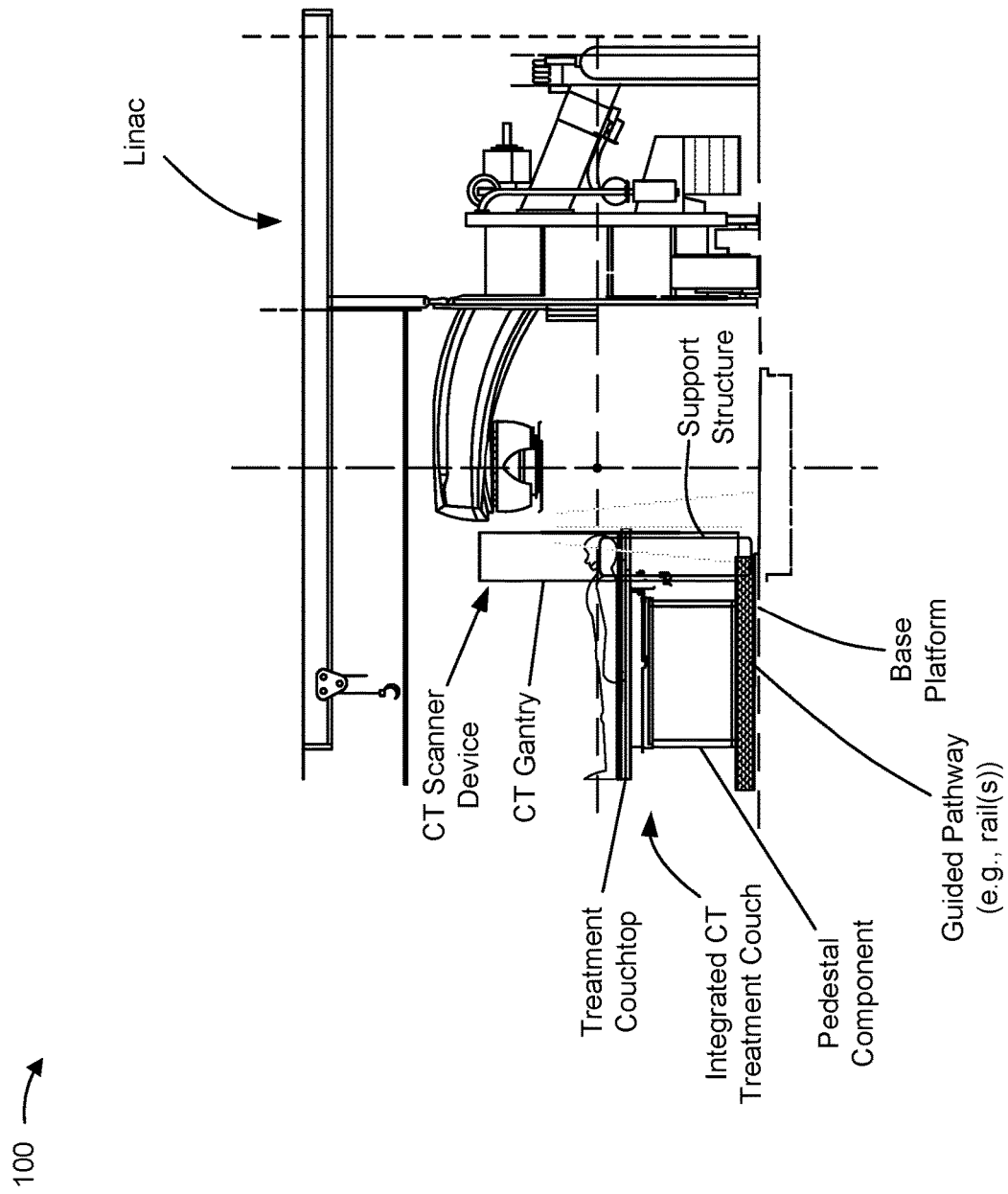
Figure 1M:
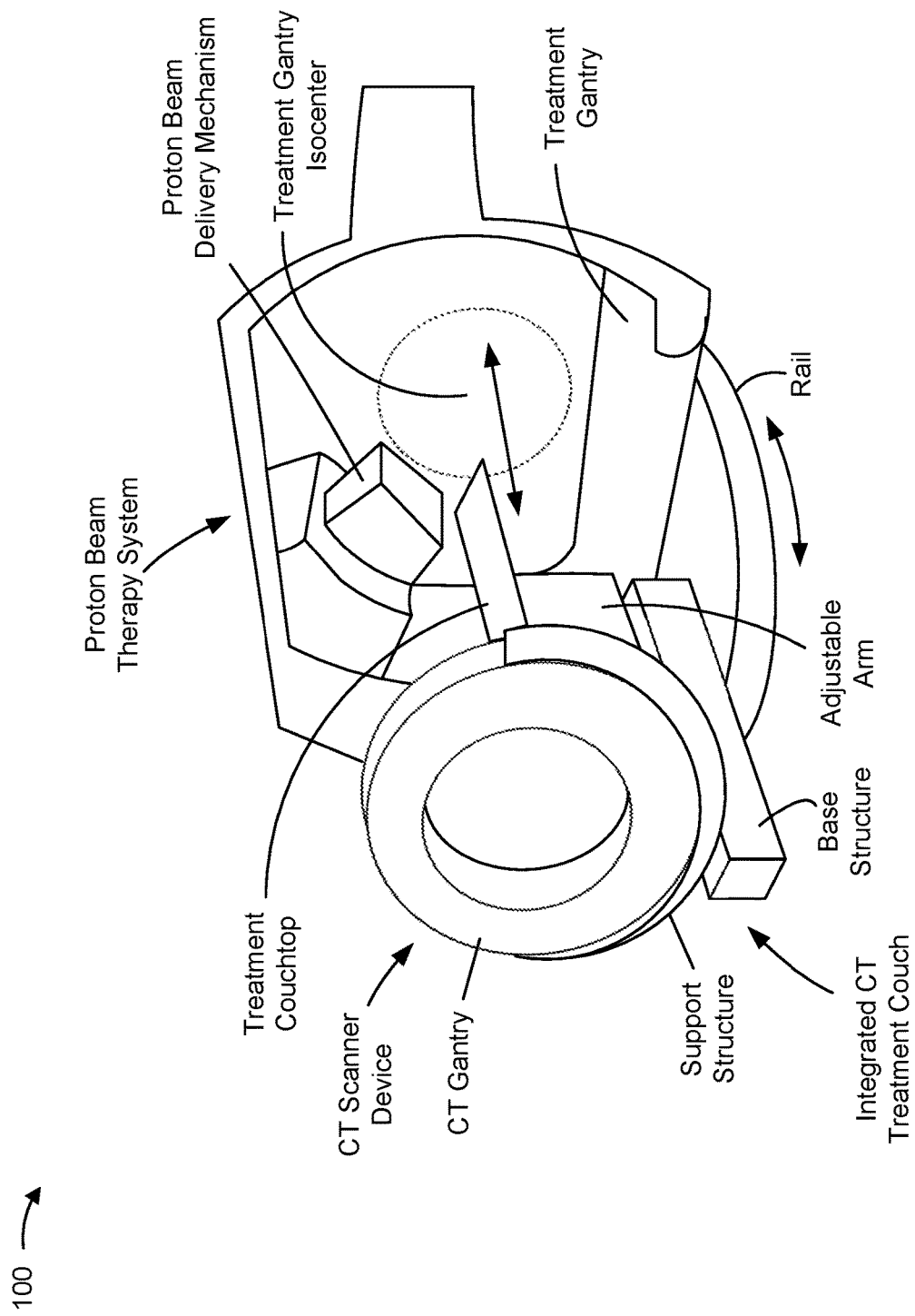
Figure 1N:
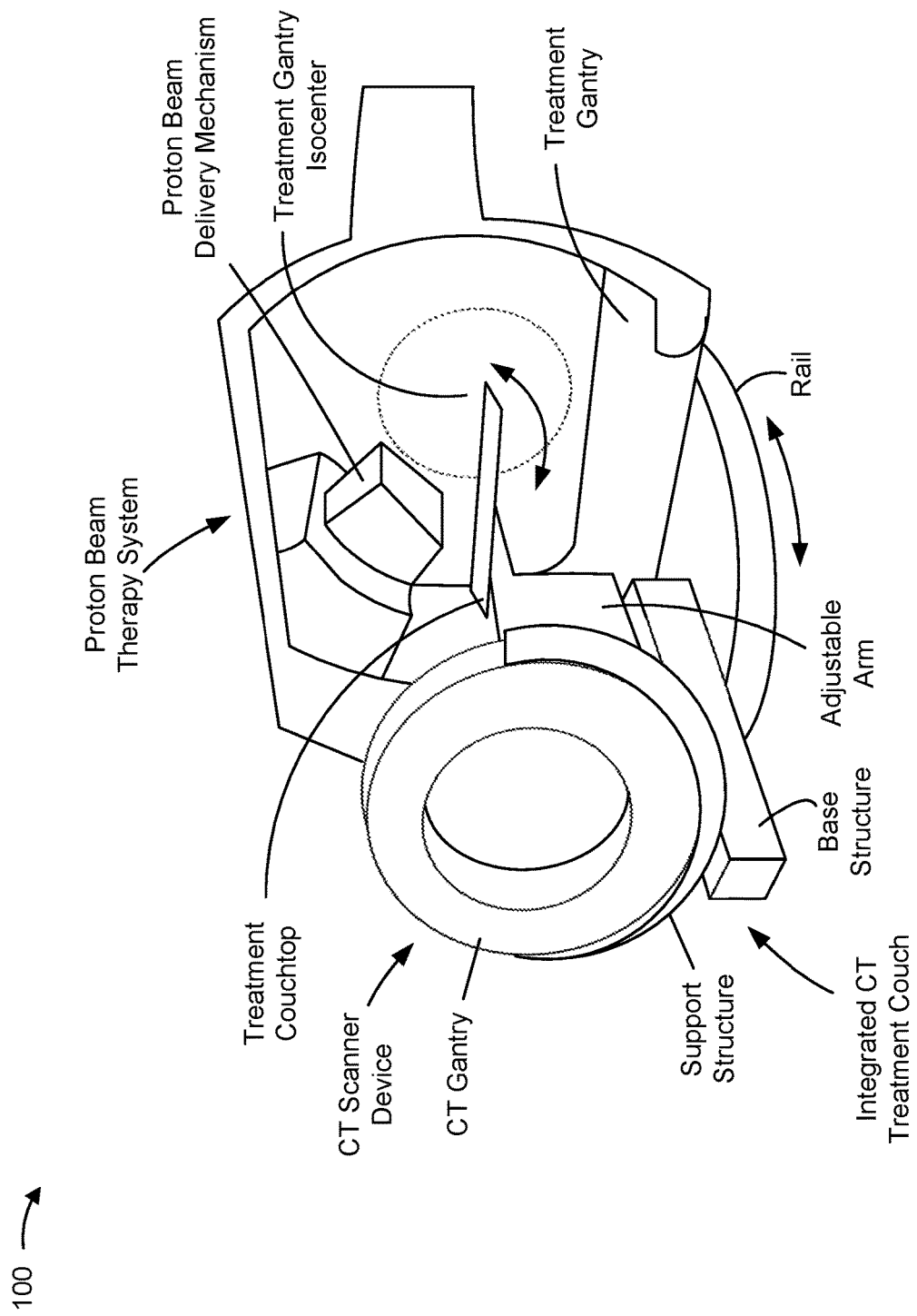

FIGS. 1A-1N are diagrams of an example implementation 100 described herein. FIG. 1A is a side view of an example integrated CT treatment couch system configured for on-line use with a linac. FIG. 1B is a front view of the example integrated CT treatment couch system and the linac. As shown in FIG. 1A, example implementation 100 may include an integrated CT treatment couch system that is aligned with a beam isocenter axis of the linac. As shown, the integrated CT treatment couch system may include a base platform, a CT scanner device—e.g., an axial or helical CT scanner device—mounted to the base platform, a pedestal component also mounted to the base platform, and a treatment couchtop disposed on the pedestal component.

In some implementations, the base platform may be configured to couple to a rotatable floor component (not shown) that is aligned with the beam isocenter axis of the linac. FIG. 1C is a top view of the example integrated CT treatment couch system and the linac, in which the integrated CT treatment couch system is positioned in a first orientation relative to the beam isocenter axis of the linac, and FIG. 1D is a top view of the example integrated CT treatment couch system and the linac, in which the integrated CT treatment couch system is positioned in a second orientation relative to the beam isocenter axis. Coupling the base platform to the rotatable floor component permits an operator to kick (e.g., rotate) both the CT scanner device and the treatment couchtop about the beam isocenter axis, which enables flexible treatment via the linac.

In some implementations, the CT scanner device may be configured to provide CT scans that provide image guidance for radiotherapy and/or that are useful for assisting with various types of procedures, including, for example, spinal radiosurgery, cranial radiosurgery, brachytherapy, and/or the like. As shown in FIG. 1A, and in some implementations, the CT scanner device may include a support structure and a CT gantry—e.g., a rotatable CT gantry (e.g., for CT scanning, in a plane (e.g., the y-z plane) that is parallel to an axis of rotation of the treatment gantry)—coupled to the support structure. In some implementations, the support structure may be mounted to the base platform via one or more coupling mechanisms. For example, the support structure may be rigidly affixed (e.g., welded and/or the like) to the base platform, fastened to the base platform via one or more fasteners (e.g., screws, bolts, nuts, and/or the like), and/or the like. Additionally, or alternatively, the support structure may be mounted to the pedestal component via one or more coupling mechanisms. In a case where the support structure is fixedly mounted to the base platform and/or the pedestal component, CT scans (e.g., volumetric CT scans) of a patient on the treatment couchtop may be obtained via translational motion of the treatment couchtop (e.g., along the z-axis through the bore of the CT gantry). In some implementations, the CT gantry may be coupled to the support structure in a manner that permits the CT gantry to tilt (e.g., in the Θyz plane shown in FIG. 1A) or translate so as to facilitate CT scanning as needed and to allow a common isocenter for imaging and treatment. The common or shared isocenter may include a physical point in space within an imaging system field of view (FOV) (e.g., nominally, but not necessarily, a center called an imaging isocenter) and within a volume of space that can be accessed by a treatment system (e.g., nominally, but not necessarily, a center called a treatment isocenter). In some implementations, the CT gantry may include one or more X-ray sources and one or more corresponding detectors arranged within an enclosure and may be configured to rotate concentrically to provide high quality axial or helical CT scans for interventional procedures.

In some implementations, the CT scanner device may be a multi-detector CT (MDCT) scanner device that includes multiple rows of detectors. For example, a MDCT scanner device may include eight, sixteen, thirty-two, sixty-four, or more rows of detectors. Incorporation of a MDCT scanner device within the CT gantry may be consistent with the axial and/or helical image acquisition modes described above.

In some implementations, operation of the integrated CT treatment couch system, including various functions of the CT scanner device, may be facilitated via motion control, sensors, and/or data connectivity. For example, although not shown, in some implementations, the integrated CT treatment couch system may include one or more motors—e.g., disposed within the pedestal component, coupled to the treatment couchtop, and/or the like—configured to control movement of the pedestal component and/or the treatment couchtop. The motor(s) may include any suitable type of motor, such as, for example, a direct current (DC)-based motor, a synchronous-based motor, an induction-based motor, and/or the like. In some implementations, the integrated CT treatment couch system may include one or more shafts and/or the like (e.g., for coupling the motor(s) and internal structural components within the pedestal component and/or portions of the treatment couchtop), one or more power sources (e.g., for powering the motor(s)), electric/ electronic circuitry (e.g., regulator(s) and/or the like), memory, and/or the like.

In some implementations, the integrated CT treatment couch system may include a processor (e.g., one or more processing devices) configured to control the motor(s). In some implementations, the processor may be configured to provide control signals to the motor(s) to cause movement of the pedestal component and/or the treatment couchtop. As an example, the processor may (e.g., based on programmed instructions, based on an input by a user, such as an operator of the integrated CT treatment couch system, and/or the like) control the motor(s) to cause the pedestal component to expand in an upward direction (e.g., to raise the treatment couchtop along a y-axis shown in FIG. 1A), cause the pedestal component to contract, or compress, in a downward direction (e.g., to lower the treatment couchtop), cause the CT device to translate relative to the treatment couchtop, cause the treatment couchtop to move translationally relative to the pedestal component and/or the base platform (e.g., along a z-axis shown in FIG. 1A), and/or the like. In some implementations, the treatment couchtop may be configured to move with six degrees of freedom (6 DOF)—along the y-axis, along the z-axis, along an x-axis (e.g., shown in FIG. 1B), and also about a pitch axis (e.g., in the $\Theta_{yz}$ plane shown in FIG. 1A), about a roll axis (e.g., about the z-axis), and about a yaw axis (e.g., in a $\Theta_{xz}$ plane shown in FIG. 1C), which permits flexible adjustment of the treatment couchtop for obtaining on-line CT scans and for facilitating patient treatment at the linac.

In some implementations, the integrated CT treatment couch system may include, or be communicatively coupled to, one or more sensors, imaging sensors, and/or non-contact monitoring systems, configured to monitor a position of the treatment couchtop (e.g., relative to the pedestal component, the CT gantry, the base platform, the ground, and/or the like), monitor a load (e.g., a weight of a patient) on the treatment couchtop, monitor a posture of a patient on the treatment couchtop and/or a position of one or more body parts of the patient while the patient is resting on the treatment couchtop, and/or the like. In some implementations, the sensor(s) may, based on such monitoring, generate sensor signals, and provide the sensor signals to the processor for processing. In some implementations, the processor may, based on the sensor signals, control the motor(s) to move the pedestal component and/or the treatment couchtop accordingly. For example, in a case where sensor signal(s) indicate that an end of the treatment couchtop is sagging downwardly (e.g., when the treatment couchtop is extended translationally in the z-axis towards a treatment gantry), such as due to a weight of a patient on the treatment couchtop, the processor may control the motor(s) to tilt the treatment couchtop (e.g., upwardly) to compensate for the sag. As another example, in a case where the sensor signal(s) indicate that a patient's body part(s) are not in a proper position (e.g., a patient's hips are not squarely positioned), the processor may control the motor(s) to roll the treatment couchtop and/or to move the treatment couchtop in yaw and/or pitch. In some implementations, sensor signal(s) and information based on on-treatment CT scans (e.g., results from comparisons of the on-treatment CT scans and previously-obtained planning CT scans) may be utilized by the processor to determine how and/or how much to adjust the treatment couchtop. For example, in some implementations, the integrated CT treatment couch system may include, or be communicatively coupled to, one or more smart sensors configured to monitor patient respiratory cycles (e.g., which may provide sensor signal(s) useful for controlling the CT scanner device in a manner that reduces respiratory motion artifacts—e.g., for "gated" or "4D" imaging), to monitor patient cardiac cycles useful for controlling the CT scanner device in a manner that reduces cardiac motion artifacts— e.g., for gated or 4D imaging of a patient's heart), and/or the like. As other example, the integrated CT treatment couch system may include video sensors for video monitoring of the treatment couchtop, electromagnetic-based sensors for tracking radio frequency transponders that might be disposed on, or in, a patient, and/or the like.

In some implementations, the processor may be configured to control (e.g., based on an input by a user, based on one or more preprogrammed CT scanning modes, and/or the like) rotation of the CT gantry (e.g., by controlling a motor in the CT gantry), the operation of the emitters and/or detectors in the CT gantry, and/or the like to provide CT scanning functions. In some implementations, the CT scanner device may be configured to provide a variety of CT scanning functionalities. For example, the CT scanner device may be configured to perform helical CT scanning (e.g., based on continuous movement of the treatment couchtop and the patient, along the z-axis through a bore of the CT gantry, during continuous rotation of the CT gantry, resulting in a helical, or spiral-like, path, of the X-ray source(s) and corresponding detector(s) of the CT scanner device, with respect to an anatomy of the patient), axial CT scans (e.g., based on step-by-step, or step-wise, movements of the treatment couchtop and the patient, along the z-axis through the bore of the CT gantry in concert with periodic rotation of the CT gantry, where image slices may be stacked to form a volume image), and/or the like. As another example, the CT scanner device may be configured to provide four-dimensional (4D) CT scanning, including 4D respiratory-correlated CT scanning (e.g., where CT scan data—e.g., obtained while the CT gantry is rotating at a continuous speed, the treatment couchtop is moving at a steady rate (e.g., in the z-axis shown in FIG. 1A), and a patient is breathing regularly—may be used to construct respiratory-gated scans), 4D cardiac CT scanning, and/or the like. As another example, the CT scanner device may be configured to facilitate CT scanning based on contrast angiography (CTA), perform at least dual energy CT scanning, and/or the like.

In some implementations, the CT gantry may have a large bore (e.g., greater than about 100 centimeters (cm) in diameter and/or the like), and may be thin in width (e.g., less than about 50 cm in width and/or the like). In some implementations, the CT scanner device may be capable of providing CT scans with a small slice thickness (e.g., about 1 millimeter (mm) in slice thickness and/or the like) and at a fast variable rate (e.g., about 20 cm of thickness of a volume in about 8 seconds and/or the like), and may have a large scan range (e.g., about 1 meter and/or the like).

In some implementations, the integrated CT treatment couch system may include one or more in-room and/or remote-based user interfaces (e.g., including a capacitive touch screen, a keypad, and/or the like) configured to enable a user (e.g., an operator) to interact with the integrated CT treatment couch system, such as to input instructions for controlling the CT gantry of the CT scanner device, for controlling movement of the treatment couchtop and/or the pedestal component, and/or the like. In some implementations, the user interface(s) may include a display configured to display information regarding the integrated CT treatment couch system (e.g., status information and/or position information regarding the treatment couchtop, the pedestal component, and/or the CT scanner device), to display CT scans obtained by the CT scanner device, and/or the like. In some implementations, the integrated CT treatment couch system may include a communication interface configured to permit data exchange with one or more external systems (e.g., external systems for performing image analysis on CT scans and/or the like).

In this way, a CT scanner device and a treatment couchtop may be controlled in synchrony to provide on-treatment diagnostic-quality CT scans in a treatment room. Additionally, arranging the integrated CT treatment couch system to be in line with a beam isocenter of a linac also permits rapid switching of a patient between treatment and CT scanning positions, which shortens treatment times, thereby conserving power resources and increasing patient throughput.

FIGS. 1E-1K are various views of example integrated CT treatment couch systems configured for use with a linac (e.g., a linac provided by Elekta AB and/or the like). The integrated CT treatment couch system may be similar to the integrated CT treatment couch system described above in connection with FIGS. 1A-1D. For example, here, as shown in FIGS. 1E-1I, the integrated CT treatment couch system may be aligned with a beam isocenter axis of the linac, and may include a base platform, a CT scanner device—e.g., a helical CT scanner device (e.g., a CT scanner device provided by Mobius Imaging and/or the like)—mounted to the base platform and/or to the pedestal component (e.g., mounted in a front-treatment implementation), and a treatment couchtop disposed on the pedestal component. As another example, the integrated CT treatment couch system may include a processor, motor(s), and/or sensor(s) similar to those described above in connection with FIGS. 1A-1D.

As shown in FIGS. 1E, 1G, and 1H, for example, and similar to the integrated CT treatment couch system described above in connection with FIGS. 1A-1D, the support structure of the CT scanner device may be mounted to the base platform and/or to the pedestal component via one or more coupling mechanisms, and CT scans (e.g., volumetric CT scans) of a patient on the treatment couchtop may be obtained via translational motion of the treatment couchtop (e.g., along the z-axis through a bore of the CT gantry).

In some implementations, the pedestal component may be compressible to lower the treatment couchtop (e.g., as shown in FIG. 1E), and expandable to raise the treatment couchtop, to facilitate patient loading and positioning for treatment. In some implementations, the treatment couchtop may additionally, or alternatively, be movable relative to the CT scanner device and/or a treatment gantry (e.g., leftward and rightward in FIG. 1E) to facilitate patient loading and positioning for treatment.

In some implementations, and as shown in FIG. 1F, for example, the overall dimensions of a CT gantry of the CT scanner device (e.g., including a bore of the CT gantry and an outer circumference/aperture of the CT gantry) may correspond, and/or align, to geometry and/or dimensions of the linac, which may avoid collisions between the CT gantry and the treatment gantry.

As shown in FIG. 1G, the treatment couchtop may be loaded with a patient (e.g., in place on a plane of the beam isocenter) and positioned through a bore of the CT gantry to permit CT scanning of a target portion of the patient. As shown in FIG. 1H, the treatment couchtop may be positioned (e.g., in an extended position) closer towards the treatment gantry to permit non-coplanar treatment of the patient via the linac. As shown in FIGS. 1E, 1G, and 1H, the base platform may be coupled to a rotatable floor component that is aligned with the beam isocenter of the linac. This permits the integrated CT treatment couch system (e.g., the CT scanner device and the treatment couchtop) to move axially about the beam isocenter to facilitate varied treatment via the linac. FIG. 1I shows the treatment couchtop and the CT scanner device in various rotated positions about the beam isocenter. As shown, both the treatment couchtop and the CT scanner device may, by virtue of being integrated with one another (e.g., via the base platform), rotate in unison when the rotatable floor component is rotated, which permits CT scanning even in cases where the treatment couchtop is moved to a different position about the beam isocenter. In some implementations, and as shown in FIG. 1I, isocentric rotation of the treatment couchtop and the CT scanner device may be limited (e.g., within a range of about −100 degrees to about +100 degrees) so as to prevent the CT gantry from contacting the treatment gantry.

In some implementations, the CT scanner device may be mounted in a different position than that shown in FIG. 1E (e.g., other than in a front-treatment position). As shown in FIG. 1J, for example, the CT scanner device may be mounted (e.g., to the base platform and/or to the pedestal component via one or more coupling mechanisms) proximate to a middle portion of the pedestal component (e.g., in a mid-treatment position). Alternatively, as shown in FIG. 1K, the CT scanner device may be mounted (e.g., to the base platform and/or to the pedestal component via one or more coupling mechanisms) proximate to an end of the pedestal component that is farthest from the linac (e.g., in an end-treatment position). In any case, and regardless of where the CT scanner device is mounted relative to the pedestal component and/or the linac, the treatment couchtop may be configured to move through the bore of the CT gantry to facilitate patient scanning, and to be positioned for patient treatment by the linac.

In some implementations, an integrated CT treatment couch system may replace an existing treatment couch without needing any change to an existing linac or particle therapy-based system. In some implementations, an existing treatment couch may be modified to arrive at an implementation of the integrated CT treatment couch system described herein. In such a case, for example, the treatment couch may be shifted away from the treatment gantry (e.g., by at least a distance that corresponds to a width of the CT gantry (e.g., by 40 cm and/or the like)) in order to accommodate the addition of the CT scanner device. In some implementations, the CT scanner device may be easily removable (e.g., from the base platform and/or the pedestal component) in times when CT scanning functionality is not needed, and may be easily reinstalled (e.g., remounted to the base platform and/or the pedestal component) as needed. In some implementations, the CT scanning functionality of the integrated CT treatment couch system (e.g., the CT scanner device) may be provided as add-on—e.g., as an optional feature of the system.

In some implementations, and as shown in FIG. 1L, the integrated CT treatment couch system may include a guided pathway (e.g., including one or more rails) coupled to, or incorporated on, the base platform, that permits the CT scanner device (e.g., the CT gantry) to move relative to the treatment couchtop. This enables CT scans (e.g., volumetric CT scans) to be obtained (e.g., in continuous helical or step-wise axial) via translational motion of only the treatment couchtop (and not of the CT gantry) (e.g., similar to that described above in connection with FIGS. 1A-1K), translational motion of only the CT gantry along the guided pathway (and not of the treatment couchtop), and/or combined translational motion of both the treatment couchtop and the CT gantry. Combined translational motion of both the treatment couchtop and the CT gantry may, for example, provide improvements in CT scan speeds and extended coverage (e.g., along the z-axis). Furthermore, by virtue of the guided pathway being coupled to, or incorporated on, the base platform, the guided pathway may also move (along with the CT scanner device) about the beam isocenter axis when the rotatable floor component is rotated (e.g., with a couch kick).

FIGS. 1M and 1N are perspective views of an example integrated CT treatment couch system configured for use in a system that provides particle therapy, such as a proton beam therapy system. As shown in FIG. 1M, a proton beam therapy system may include a 360° rotating treatment gantry and a proton beam delivery mechanism. As shown, the integrated CT treatment couch system may include a base structure, an adjustable arm coupled to the base structure, and a treatment couchtop disposed on the adjustable arm. As shown, the integrated CT treatment couch system may also include a CT scanner device having a support structure mounted to the base structure (e.g., at or proximate to a portion of the base structure to which the adjustable arm is coupled), and a CT gantry. In some implementations, the CT gantry may include a bore, may be oriented such that the bore is in line with the treatment couchtop, and may be configured to generate on-line helical CT scans, as described above in connection with FIGS. 1A-1L.

In some implementations, and as shown in FIG. 1M, the base structure may be configured to traverse one or more guided pathways (e.g., rails or race-rails) that are disposed on the ground, or floor, and aligned with a gantry isocenter of the proton beam therapy system. For example, in some implementations, the base structure may include one or more wheels and/or may include a surface having a low coefficient of friction, which enables the base structure to traverse the guided pathway(s). This permits rotation of the CT scanner device to accommodate for intraoperative CT scanning as needed. In some implementations, and as shown in FIG. 1N, the treatment couchtop may be configured to rotate about an axis to permit various treatment positions.

In some implementations, the integrated CT treatment couch system may include one or more motors, a processor, one or more sensors, and/or the like, similar to those described above in connection with FIGS. 1A-1L, for controlling movement of the adjustable arm, for controlling traversal of the integrated CT treatment couch system along the guided pathway(s), for controlling movement of the treatment couchtop (e.g., with 6 DOF), for controlling the CT scanner device to provide CT scans, and/or the like.

In some implementations, optical, infrared, and/or other forms of non-contact systems that may be used to monitor patient position during treatment may be mounted in and/or integrated with the integrated CT treatment couch system described herein. In some implementations, technical advances in software (e.g., such as advanced reconstruction software) and hardware (e.g., such as multi-energy or spectral scanning), that are made on present and future diagnostic CT scanners may be incorporated in the integrated CT treatment couch system described herein. In some implementations, the integrated CT treatment couch system may enable development of new intensity-modulated radiation therapy (IMRT) and/or new extended length delivery approaches with computer-controlled CT couch motion.

The integrated CT treatment couch system may include an additional ring-panel of nuclear medicine-type detectors (e.g., lutetium oxyorthosilicate (LSO) detectors) on the couch to enable low-cost positron-emission tomography (PET) or single-photon emission computed tomography (SPECT) guidance for the integrated CT treatment couch system.

In this way, on-treatment diagnostic-quality CT scans (or helical CT quality scans) for IGRT and/or treatment planning may be obtained, in a treatment room, via CT scanner capabilities provided onboard a treatment couch. Integrating a CT scanner device that is capable of providing helical CT scans, rather than CBCT-based scans (as are typically used in the treatment room), yields higher quality CT scans, and permits faster CT scan speeds. Additionally, providing an integrated CT scanner device on a treatment couch system also reduces or eliminates a need to include, or utilize, a CBCT-based scanner on a treatment gantry of a linac, reduces or eliminates a need for such a CBCT-based scanner to be folded away during treatment (as is required if oblique or non-coplanar beam arrangements of the linac are needed for treatment purposes), and/or allows the use of a smaller imaging panel for the sole purpose of kilovoltage (kV) radiographic or fluoroscopic imaging. This conserves costs, improves the IGRT process, shortens treatment times, and increases overall patient throughput. Furthermore, integrating the CT scanner device and the treatment couchtop (e.g., which may simply replace an existing treatment couch), such that both the CT scanner device and the treatment couchtop are rotatable (e.g., as an integrated unit) about a beam isocenter axis of a typical linac, also permits non-coplanar capabilities of the linac to be retained without requiring any overhaul, or costly changes, to be made to the linac (this is, for example, in contrast to recently-proposed advanced treatment machines, which all sacrifice the non-coplanar capabilities by eliminating couch rotation capabilities in favor of improved imaging). Moreover, utilizing an integrated CT scanner device also reduces or eliminates a need to arrange for, and utilize, a typical standalone CT scanning system for IGRT purposes. For example, use of a standalone CT scanner configuration, such as one in which the CT gantry is movable on rails (e.g., a CT-on-rails system in the treatment room), would involve additional patient motion in the treatment room (e.g., including turning a conventional treatment couch toward the CT gantry for CT scanning, and then turning the conventional treatment couch back in line with the linac for patient treatment). This involves manual effort and additional time—e.g., time during which the patient may move (e.g., including internal organ motion and/or the like), which may affect the treatment procedure. In contrast, having an integrated CT scanner device that remains in line with the treatment couchtop and the patient, even when the treatment couchtop is moved (e.g., with a couch kick), as described herein, simplifies switching between CT scanning and patient treatment in the treatment room, which shortens treatment times and increases overall patient throughput.

As indicated above, FIGS. 1A-1N are provided merely as examples. Other examples may differ from what was described with regard to FIGS. 1A-1N. For example, although implementations of the integrated CT treatment couch system are described herein as being configured for use with radiotherapy and/or proton beam-based therapy, implementations of the integrated CT treatment couch system may be configured for use with other forms of therapy, such as neutron-based therapy, charged ion-based therapy, and/or the like.

Figure 2:
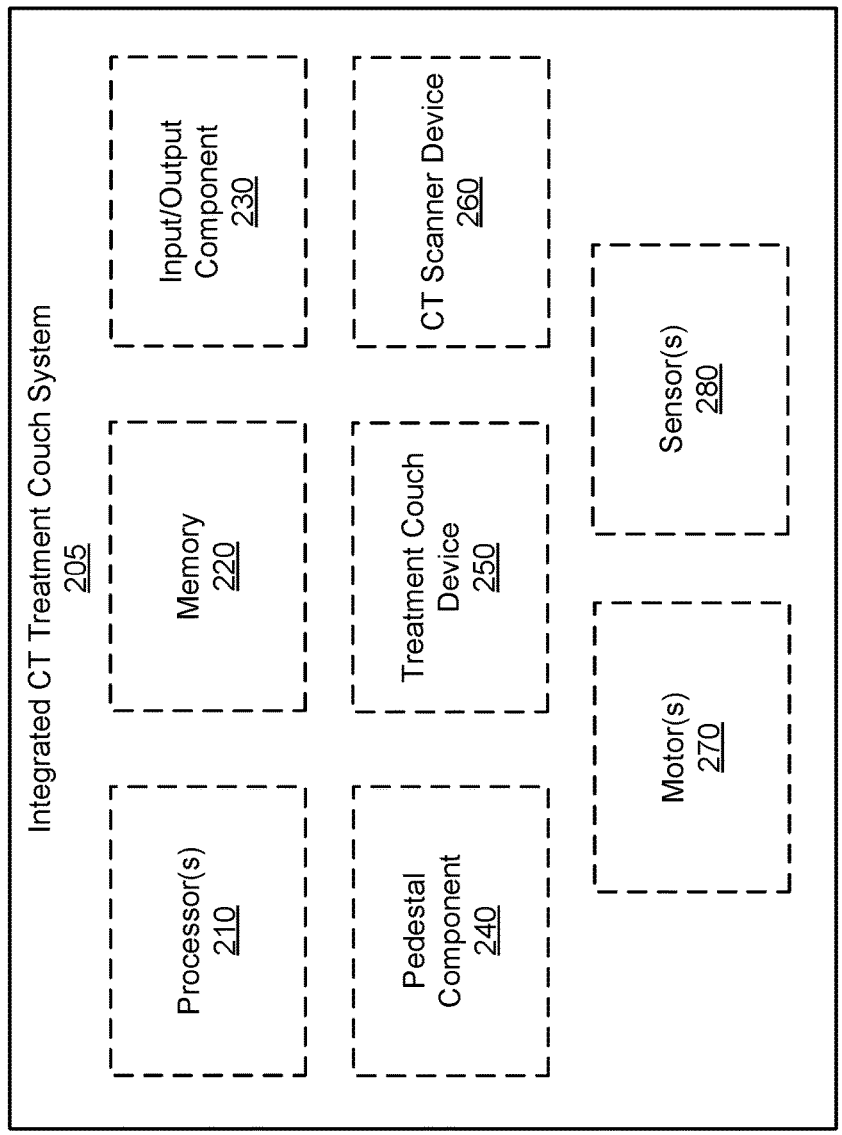
FIG. 2 is a diagram of an example environment in which systems and/or methods, described herein, may be implemented.

FIG. 2 is a diagram of an example environment 200 in which systems and/or methods, described herein, may be implemented. As shown in FIG. 2, environment 200 may include an integrated CT treatment couch system 205 that includes various components and/or devices. Devices of environment 200 may interconnect via wired connections, wireless connections, or a combination of wired and wireless connections.

Integrated CT treatment couch system 205 includes one or more devices capable of supporting a patient for interventional procedures and providing on-line diagnostic CT scans for guiding such procedures.

Processor(s) 210 include one or more types of processing components capable of being programmed to perform a function, such as one or more operations described elsewhere herein. For example, processor(s) 210 may perform process 400 of FIG. 4 and/or the like. In some implementations, processor(s) 210 may include a processor configured to control one or more motor(s) (e.g., motor(s) 270) for controlling a pedestal component (e.g., pedestal component 240), a treatment couchtop (e.g., treatment couchtop 250), and/or a CT scanner device (e.g., CT scanner device 260), as described elsewhere herein. Processor(s) 210 corresponds to a processor, described in more detail below in connection with FIG. 3.

Memory 220 includes one or more types of memories capable of storing information. In some implementations, memory 220 may store information associated with performing one or more operations described elsewhere herein. For example, memory 220 may store information to be used (e.g., by processor(s) 210) to perform process 400 of FIG. 4 and/or the like. In some implementations, memory 220 may correspond to a memory or storage component, described in more detail below in connection with FIG. 3.

Input/output component 230 includes one or more components capable of being used to input information into, and/or output information from, integrated CT treatment couch system 205. In some implementations, input/output component 230 may include one or more touch screen components, one or more keypads, and/or the like. In some implementations, input/output component 230 may include one or more user interfaces configured to permit an operator to interact with integrated CT treatment couch system 205 and/or view CT scans provided by CT scanner device 260, as described elsewhere herein. In some implementations, input/output component 230 may correspond to an input component and an output component, described in more detail below in connection with FIG. 3.

Pedestal component 240 includes one or more devices configured to provide support and/or control movement of treatment couchtop 250. In some implementations, pedestal component 240 may compress and/or expand (e.g., vertically) so as to move treatment couchtop 250 up and down, as described elsewhere herein. In some implementations, pedestal component 240 may include motor(s) 270 for moving treatment couchtop 250 in a variety of directions, as described elsewhere herein.

Treatment couchtop 250 includes one or more devices that provide one or more surfaces upon which a patient may rest during a treatment procedure, such as radiotherapy. In some implementations, treatment couchtop 250 may be configured to move in 6 DOF, as described elsewhere herein. In some implementations, treatment couchtop 250 may be integrated with one or more external devices, such as an ultrasound imaging assembly, that may provide information regarding internal features of a patient during treatment, where beams (e.g., from the CT scanning) may, or may not, interfere with the operation of such external devices.

CT scanner device 260 includes one or more devices capable of generating CT scans. For example, CT scanner device 260 may include a support structure configured to couple to pedestal component 240 (and/or to a base platform upon which pedestal component 240 may be disposed), and a rotating CT gantry that includes one or more emitters (e.g., X-ray emitters) and detectors (e.g., X-ray detectors) for obtaining CT scans, as described elsewhere herein.

Motor(s) 270 include one or more devices capable of controlling movement of pedestal component 240 and/or treatment couchtop 250, as described elsewhere herein. In some implementations, motor(s) 270 may include any suitable type of motor, such as, for example, a DC-based motor, a synchronous-based motor, an induction-based motor, and/or the like, that is controllable by processor(s) 210 to move pedestal component 240 and/or treatment couchtop 250, as described elsewhere herein.

Sensor(s) 280 include one or more devices capable of sensing motion, position, and/or the like associated with pedestal component 240, treatment couchtop 250, and/or a patient resting on treatment couchtop 250. For example, sensor(s) 280 may include one or more motion sensors (e.g., accelerometers, gyroscopes, and/or the like), position sensors, weight sensors, and/or the like. In some implementations, sensor(s) 280 may provide sensor signals to processor(s) 210 to facilitate control of pedestal component 240 and/or treatment couchtop 250, as described elsewhere herein.

The number and arrangement of devices and components shown in FIG. 2 are provided as an example. In practice, there may be additional devices and/or components, fewer devices and/or components, different devices and/or components, or differently arranged devices and/or components than those shown in FIG. 2. Furthermore, two or more devices or component shown in FIG. 2 may be implemented within a single device or component, or a single device or component shown in FIG. 2 may be implemented as multiple, distributed devices or components. Additionally, or alternatively, a set of devices or components of environment 200 may perform one or more functions described as being performed by another set of devices or components of environment 200.

Figure 3:
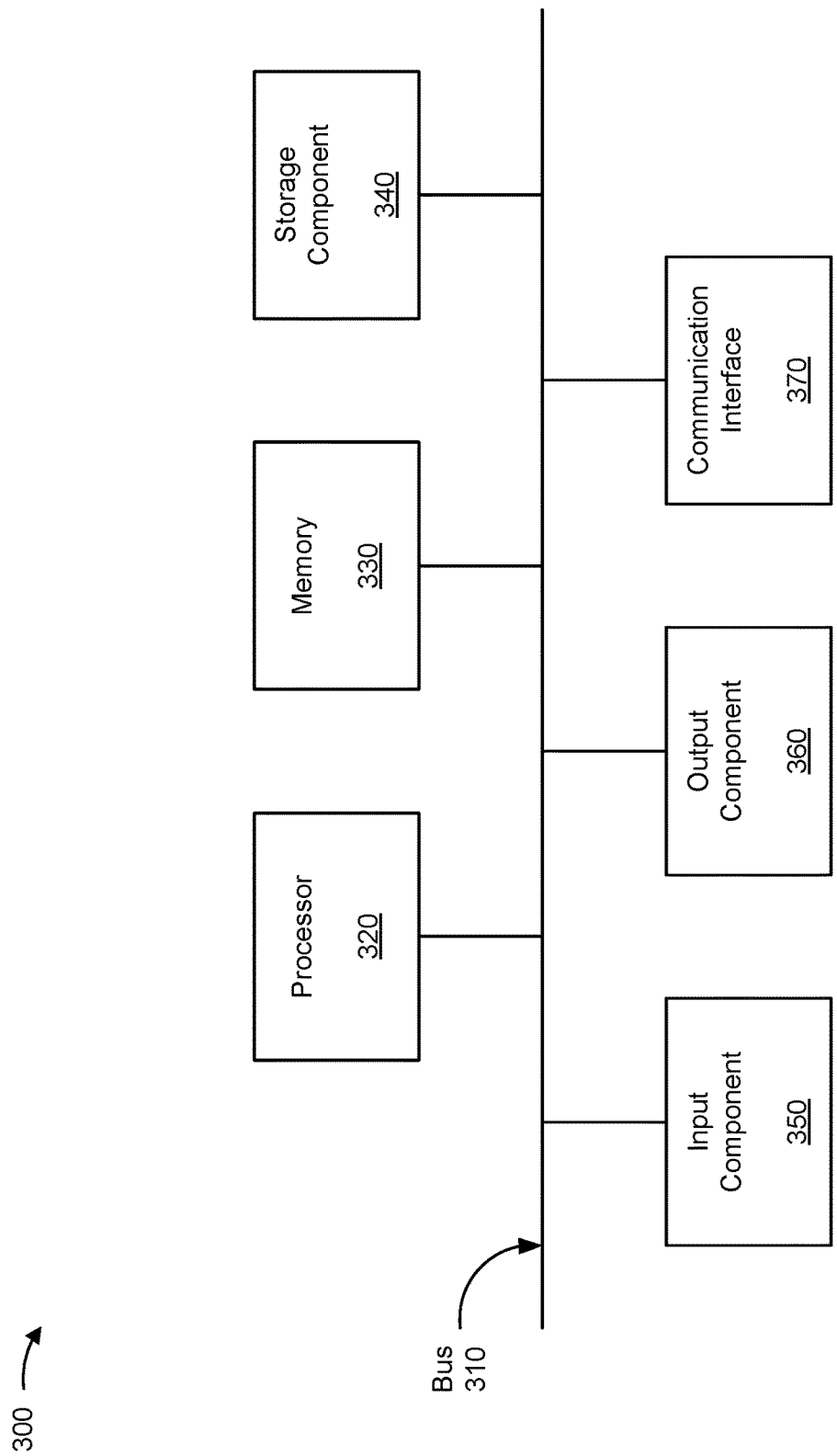
FIG. 3 is a diagram of example components of one or more devices of FIG. 2.

FIG. 3 is a diagram of example components of a device 300. Device 300 may correspond to integrated CT treatment couch system 205. In some implementations, integrated CT treatment couch system 205 may include one or more devices 300 and/or one or more components of device 300. As shown in FIG. 3, device 300 may include a bus 310, a processor 320, a memory 330, a storage component 340, an input component 350, an output component 360, and a communication interface 370.

Bus 310 includes a component that permits communication among the components of device 300. Processor 320 is implemented in hardware, firmware, or a combination of hardware and software. Processor 320 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some implementations, processor 320 includes one or more processors capable of being programmed to perform a function. Memory 330 includes a random-access memory (RAM), a read only memory (ROM), and/or another type of dynamic or static storage device (e.g., a flash memory, a magnetic memory, and/or an optical memory) that stores information and/or instructions for use by processor 320.

Storage component 340 stores information and/or software related to the operation and use of device 300. For example, storage component 340 may include a hard disk (e.g., a magnetic disk, an optical disk, a magneto-optic disk, and/or a solid-state disk), a compact disc (CD), a digital versatile disc (DVD), a floppy disk, a cartridge, a magnetic tape, and/or another type of non-transitory computer-readable medium, along with a corresponding drive.

Input component 350 includes a component that permits device 300 to receive information, such as via user input (e.g., a touch screen display, a keyboard, a keypad, a mouse, a button, a switch, and/or a microphone). Additionally, or alternatively, input component 350 may include a sensor for sensing information (e.g., a global positioning system (GPS) component, an accelerometer, a gyroscope, and/or an actuator). Output component 360 includes a component that provides output information from device 300 (e.g., a display, a speaker, and/or one or more LEDs).

Communication interface 370 includes a transceiver-like component (e.g., a transceiver and/or a separate receiver and transmitter) that enables device 300 to communicate with other devices, such as via a wired connection, a wireless connection, or a combination of wired and wireless connections. Communication interface 370 may permit device 300 to receive information from another device and/or provide information to another device. For example, communication interface 370 may include an Ethernet interface, an optical interface, a coaxial interface, an infrared interface, a radio frequency (RF) interface, a universal serial bus (USB) interface, a wireless local area network interface, a cellular network interface, and/or the like.

Device 300 may perform one or more processes described herein. Device 300 may perform these processes based on processor 320 executing software instructions stored by a non-transitory computer-readable medium, such as memory 330 and/or storage component 340. A computer-readable medium is defined herein as a non-transitory memory device. A memory device includes memory space within a single physical storage device or memory space spread across multiple physical storage devices.

Software instructions may be read into memory 330 and/or storage component 340 from another computer-readable medium or from another device via communication interface 370. When executed, software instructions stored in memory 330 and/or storage component 340 may cause processor 320 to perform one or more processes described herein. Additionally, or alternatively, hardwired circuitry may be used in place of or in combination with software instructions to perform one or more processes described herein. Thus, implementations described herein are not limited to any specific combination of hardware circuitry and software.

The number and arrangement of components shown in FIG. 3 are provided as an example. In practice, device 300 may include additional components, fewer components, different components, or differently arranged components than those shown in FIG. 3. Additionally, or alternatively, a set of components (e.g., one or more components) of device 300 may perform one or more functions described as being performed by another set of components of device 300.

FIG. 4 is a flow chart of an example process 400 for controlling an integrated CT treatment couch system. In some implementations, one or more process blocks of FIG. 4 may be performed by an integrated CT treatment couch system (e.g., integrated CT treatment couch system 205). In some implementations, one or more process blocks of FIG. 4 may be performed by another device or a group of devices separate from or including the integrated CT treatment couch system. In some implementations, the integrated CT treatment couch system may include a base platform, a pedestal component mounted to the base platform, a treatment couchtop disposed on the pedestal component, and a CT scanner device. In some implementations, the CT scanner device may include a support structure and a CT gantry. In some implementations, the support structure may be coupled to the base platform or to the pedestal component. In some implementations, the CT gantry may have a bore, and may be oriented such that the bore is in line with the treatment couchtop. In some implementations, the CT gantry may be configured to provide image guidance for radiotherapy. In some implementations, the integrated CT treatment couch system may include one or more sensors configured to generate position information.

As shown in FIG. 4, process 400 may include monitoring position information relating to the integrated CT treatment couch system and/or relating to a patient utilizing the integrated CT treatment couch system (block 410). For example, the integrated CT treatment couch system (e.g., using processor(s) 210, memory 220, sensor(s) 280, processor 320, memory 330, storage component 340, and/or the like) may monitor position information relating to the integrated CT treatment couch system and/or relating to a patient utilizing the integrated CT treatment couch system, as described above in connection with FIGS. 1A-1N.

As further shown in FIG. 4, process 400 may include controlling, by the integrated CT treatment couch system, movement of the treatment couchtop based on the position information (block 420). For example, the integrated CT treatment couch system (e.g., using processor(s) 210, memory 220, motor(s) 270, processor 320, memory 330, storage component 340, communication interface 370, and/or the like) may control movement of the treatment couchtop based on the position information, as described above in connection with FIGS. 1A-1N.

Process 400 may include additional implementations, such as any single implementation or any combination of implementations described below and/or in connection with one or more other processes described elsewhere herein.

In some implementations, the CT scanner device may be configured to provide helical CT scans based on continuous movement of the treatment couchtop through the bore of the CT gantry. In some implementations, the CT scanner device may be configured to provide axial based CT scans based on step-by-step movements of the treatment couchtop through the bore of the CT gantry. In some implementations, the CT scanner device may be configured to provide four-dimensional (4D) respiratory-based CT scanning and/or 4D cardiac-based CT scanning. In some implementations, the CT scanner device may be configured to facilitate CT angiography. In some implementations, the CT scanner device may be configured to provide dual energy CT scanning.

In some implementations, an integrated computed tomography (CT) treatment couch system may include a base platform configured to couple to a rotatable floor component associated with a medical accelerator, a pedestal component mounted to the base platform, a treatment couchtop disposed on the pedestal component, and a CT scanner device. In some implementations, the CT scanner device may include a support structure and a CT gantry. In some implementations, the CT gantry may have a bore, and may be oriented such that the bore is in line with the treatment couchtop. In some implementations, the CT gantry may be configured to generate on-line CT scans to guide radiotherapy provided by the medical accelerator. In some implementations, the support structure may be mounted to the base platform or to the pedestal component, in which volumetric CT scans of a patient on the treatment couchtop are obtained via translational motion of the treatment couchtop along an axis passing through the bore of the CT gantry, or may be configured to traverse a guided pathway coupled to, or incorporated on, the base platform, in which volumetric CT scans are obtained via translational motion of the treatment couchtop along the axis without translational motion of the CT gantry along the axis, translational motion of the CT gantry via the guided pathway along the axis without translational motion of the treatment couchtop along the axis, or combined translational motion of the treatment couchtop along the axis and the CT gantry via the guided pathway along the axis.

In some implementations, the pedestal component may be mounted to a first portion of the base platform, and the support structure may be mounted to a second portion, of the base platform, proximate to the first portion. In some implementations, a bridge structure may be coupled to the pedestal component. In some implementations, the support structure may be mounted to the pedestal component via the bridge structure.

In some implementations, the CT scanner device and the treatment couchtop may rotate about a beam isocenter of the medical accelerator when the base platform is coupled to, and rotated by, the rotatable floor component.

In some implementations, the pedestal component may include a plurality of motors coupled to the treatment couchtop. In some implementations, the plurality of motors may be configured to permit the treatment couchtop to move with six degrees of freedom (DOF).

In some implementations, the integrated CT treatment couch system may include at least one sensor configured to monitor a position of the treatment couchtop and/or a position of a patient on the treatment couchtop, and generate sensor signals based on monitoring the position of the treatment couchtop and/or the position of the patient. In some implementations, the integrated CT treatment couch system may include one or more memories, and one or more processors, communicatively coupled to the one or more memories and the at least one sensor, configured to control movement of the treatment couchtop and/or the pedestal component based on the sensor signals. In some implementations, the at least one sensor may be configured to monitor the position of the treatment couchtop by detecting a weight of the patient on the treatment couchtop. In some implementations, the at least one sensor may be configured to monitor the position of the patient by detecting a position of one or more body parts of the patient and/or a posture of at least a portion of the patient.

In some implementations, the treatment couchtop may be configured to move about a pitch axis, a roll axis, and/or a yaw axis. In some implementations, the treatment couchtop may be configured to move along an axis of the bore of the CT scanner device, move vertically relative to the axis, and/or move laterally.

In some implementations, an integrated computed tomography (CT) treatment couch system may include a robotic arm component that includes a base structure, and an adjustable arm mounted to a portion of the base structure. In some implementations, the integrated CT treatment couch system may include a treatment couch disposed on, and coupled to, the adjustable arm. In some implementations, the treatment couch may be configured to support a patient for a particle therapy procedure. In some implementations, the integrated CT treatment couch system may include a helical CT scanner device that includes a support structure and a CT gantry. In some implementations, the support structure may be coupled to the base structure at, or proximate to, the portion of the base structure. In some implementations, the CT gantry may have a bore, and may be oriented such that the bore is in line with the treatment couch. In some implementations, the CT gantry may be configured to provide on-line CT scans for image guidance relating to the particle therapy procedure.

In some implementations, the particle therapy procedure may include a proton-based therapy procedure and/or a charged ion-based therapy procedure. In some implementations, the base structure may be configured to traverse one or more rails to enable the CT scanner device to move at least partially about an area in which the particle therapy procedure is being performed.

Although FIG. 4 shows example blocks of process 400, in some implementations, process 400 may include additional blocks, fewer blocks, different blocks, or differently arranged blocks than those depicted in FIG. 4. Additionally, or alternatively, two or more of the blocks of process 400 may be performed in parallel.

In this way, online CT scans (axial or helical CT quality scans) for IGRT and/or treatment planning may be obtained, in a treatment room, via CT scanner capabilities provided onboard a treatment couch. Integrating a CT scanner device that is capable of providing axial or helical CT scans, rather than CBCT-based scans (as are typically used in the treatment room), yields higher quality CT scans, and permits faster CT scan speeds. Additionally, providing an integrated CT scanner device on a treatment couch system also reduces or eliminates a need to include, or utilize, a CBCT-based scanner on a treatment gantry of a linac, reduces or eliminates a need for such a CBCT-based scanner to be folded away during treatment (as is required if oblique or non-coplanar beam arrangements of the linac with a "couch kick" are needed for treatment purposes), and/or allows the use of a smaller imaging panel for the purpose of kilovoltage (kV) radiographic or fluoroscopic imaging. This conserves costs, improves the IGRT process, shortens treatment times, and increases overall patient throughput. Furthermore, integrating the CT scanner device and the treatment couchtop (e.g., which may simply replace an existing treatment couch), such that both the CT scanner device and the treatment couchtop can be rotated (e.g., as an integrated unit) about a beam isocenter axis of a typical linac, also permits non-coplanar capabilities of the linac to be retained without requiring any overhaul, or costly changes, to be made to the linac (this is, for example, in contrast to recently-proposed advanced treatment machines, which all sacrifice the non-coplanar capabilities by eliminating couch rotation capabilities in favor of improved imaging). Moreover, utilizing an integrated CT scanner device also reduces or eliminates a need to arrange for, and utilize, a typical standalone CT scanning system for IGRT purposes. For example, use of a standalone CT scanner configuration, such as one in which the CT gantry is movable on rails (e.g., a CT-on-rails system in the treatment room), would involve additional patient motion in the treatment room (e.g., including turning a conventional treatment couch toward the CT gantry for CT scanning, and then turning the conventional treatment couch back in line with the linac for patient treatment). This involves manual effort and additional time—e.g., time during which the patient may move (e.g., including internal organ motion and/or the like), which may affect the treatment procedure. In contrast, having an integrated CT scanner device that remains in line with the treatment couchtop and the patient, even when the treatment couchtop is moved (e.g., with a couch kick), as described herein, simplifies switching between CT scanning and patient treatment in the treatment room, which shortens treatment times and increases overall patient throughput.

The foregoing disclosure provides illustration and description, but is not intended to be exhaustive or to limit the implementations to the precise form disclosed. Modifications and variations may be made in light of the above disclosure or may be acquired from practice of the implementations.

As used herein, the term "component" is intended to be broadly construed as hardware, firmware, or a combination of hardware and software.

Some implementations are described herein in connection with thresholds. As used herein, satisfying a threshold may refer to a value being greater than the threshold, more than the threshold, higher than the threshold, greater than or equal to the threshold, less than the threshold, fewer than the threshold, lower than the threshold, less than or equal to the threshold, equal to the threshold, and/or the like.

It will be apparent that systems and/or methods, described herein, may be implemented in different forms of hardware, firmware, or a combination of hardware and software. The actual specialized control hardware or software code used to implement these systems and/or methods is not limiting of the implementations. Thus, the operation and behavior of the systems and/or methods were described herein without reference to specific software code—it being understood that software and hardware may be designed to implement the systems and/or methods based on the description herein.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items, and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," and/or the like are intended to be open-ended terms. Further, the phrase "based on" is intended to mean "based, at least in part, on" unless explicitly stated otherwise.

What is claimed is:
1. An integrated computed tomography (CT) treatment couch system, comprising:
   a base platform configured to couple to a rotatable floor component associated with a medical accelerator;
   a pedestal component mounted to the base platform;
   a treatment couchtop disposed on the pedestal component; and
   a CT scanner device,
      the CT scanner device including a support structure and a CT gantry,
      the CT scanner device being configured to rotate around a beam isocenter of the medical accelerator based on the rotatable floor component,
      the treatment couchtop being configured to move horizontally and independently of the pedestal component, to move a subject past the CT gantry and towards the beam isocenter,
      the pedestal component and the base platform are not below the beam isocenter when the treatment couchtop is moved horizontally for the subject to arrive at the beam isocenter, and
      the CT scanner device being configured to move horizontally and independently of the pedestal component, from one end of the pedestal component to an opposite end of the pedestal component and past the pedestal component,
      the CT gantry having a bore, and being oriented such that the bore is in line with the treatment couchtop, the CT gantry being configured to generate on-line CT scans to guide radiotherapy provided by the medical accelerator, and the support structure being:
mounted to the base platform or to the pedestal component, in which axial, helical, and/or volumetric CT scans of a patient on the treatment couchtop are obtained via translational motion of the treatment couchtop along an axis passing through the bore of the CT gantry, or configured to traverse a guided pathway coupled to, or incorporated on, the base platform, in which volumetric CT scans are obtained via:
translational motion of the treatment couchtop along the axis without translational motion of the CT gantry along the axis,
translational motion of the CT gantry via the guided pathway along the axis without translational motion of the treatment couchtop along the axis, or
combined translational motion of the treatment couchtop along the axis and the CT gantry via the guided pathway along the axis.

2. The integrated CT treatment couch system of claim 1, wherein the pedestal component is mounted to a first portion of the base platform, and the support structure is mounted to a second portion, of the base platform, proximate to the first portion.

3. The integrated CT treatment couch system of claim 1, wherein the support structure is mounted to the base platform and/or to the pedestal component via one or more coupling mechanisms.

4. The integrated CT treatment couch system of claim 1, wherein the CT scanner device and the treatment couchtop rotate about the beam isocenter of the medical accelerator when the base platform is coupled to, and rotated by, the rotatable floor component.

5. The integrated CT treatment couch system of claim 1, wherein the pedestal component includes a plurality of motors coupled to the treatment couchtop.

6. The integrated CT treatment couch system of claim 5, wherein the plurality of motors is configured to permit the treatment couchtop to move with six degrees of freedom (DOF).

7. The integrated CT treatment couch system of claim 1, further comprising:
at least one sensor configured to:
monitor a position of the treatment couchtop and/or a position of a patient on the treatment couchtop, and
generate sensor signals based on monitoring the position of the treatment couchtop and/or the position of the patient;
one or more memories; and
one or more processors, communicatively coupled to the one or more memories and the at least one sensor, configured to:
control movement of the treatment couchtop and/or the pedestal component based on the sensor signals.

8. The integrated CT treatment couch system of claim 7, wherein the at least one sensor is configured to monitor the position of the treatment couchtop by detecting a weight of the patient on the treatment couchtop.

9. The integrated CT treatment couch system of claim 7, wherein the at least one sensor is configured to monitor the position of the patient by detecting a position of one or more body parts of the patient and/or a posture of at least a portion of the patient.

10. The integrated CT treatment couch system of claim 1, wherein the treatment couchtop is configured to move about:
a pitch axis,
a roll axis, and/or
a yaw axis.

11. The integrated CT treatment couch system of claim 1, wherein the CT gantry is configured to tilt and the treatment couchtop is configured to move along any of three orthogonal axes, including:
a y-axis,
an x-axis, or
a z-axis.

12. The integrated CT treatment couch system of claim 1, wherein the guided pathway includes one or more rails.

13. A method, comprising:
monitoring, by an integrated computed tomography (CT) treatment couch system, position information relating to the integrated CT treatment couch system and/or relating to a patient utilizing the integrated CT treatment couch system,
the integrated CT treatment couch system including:
a rotatable base platform,
a pedestal component mounted to the rotatable base platform,
a treatment couchtop disposed on the pedestal component,
a CT scanner device,
the CT scanner device including a support structure and a CT gantry,
the support structure being coupled to the base platform or to the pedestal component,
the CT scanner device being configured to rotate around a beam isocenter of a medical accelerator based on the rotatable base platform,
the treatment couchtop being configured to move horizontally and independently of the pedestal component, to move a subject past the CT gantry and towards the beam isocenter,
the pedestal component and the rotatable base platform are not below the beam isocenter when the treatment couchtop is moved horizontally for the subject to arrive at the beam isocenter, and
the CT scanner device being configured to move horizontally and independently of the pedestal component, from one end of the pedestal component to an opposite end of the pedestal component and past the pedestal component,
the CT gantry having a bore, and being oriented such that the bore is in line with the treatment couchtop,
the CT gantry being configured to provide image guidance for radiotherapy, and
one or more sensors configured to generate the position information; and
controlling, by the integrated CT treatment couch system, movement of the treatment couchtop based on the position information.

14. The method of claim 13, wherein the CT scanner device is configured to provide helical CT scans based on continuous movement of the treatment couchtop through the bore of the CT gantry.

15. The method of claim 13, wherein the CT scanner device is configured to provide axial-based CT scans based on step-by-step movements of the treatment couchtop through the bore of the CT gantry.

16. The method of claim 13, wherein the CT scanner device is configured to provide, via helical CT scanning and/or axial-based CT scanning, four-dimensional (4D) respiratory-based CT scanning and/or 4D cardiac-based CT scanning based on gating information obtained from the one or more sensors, from one or more respiratory-based sensors, from one or more cardiac-based sensors, and/or from one or more motion sensors.

17. The method of claim 13, wherein the CT scanner device is configured to provide, via helical CT scanning and/or axial-based CT scanning, at least dual energy CT scanning and/or spectral CT scanning.

18. A computed tomography (CT) scanner device for an integrated computed tomography (CT) treatment couch system that includes a base platform configured to couple to a rotatable floor component associated with a medical accelerator, a pedestal component mounted to the base platform, and a treatment couchtop disposed on the pedestal component, the CT scanner device comprising:
a support structure; and
a CT gantry,
the CT gantry including a bore and being oriented such that the bore is in line with the treatment couchtop,
the CT gantry being configured to rotate around a beam isocenter of the medical accelerator based on the rotatable floor component,
the treatment couchtop being configured to move horizontally and independently of the pedestal component, to move a subject past the CT gantry and towards the beam isocenter,
the pedestal component and the base platform are not below the beam isocenter when the treatment couchtop is moved horizontally for the subject to arrive at the beam isocenter, and
the CT scanner device being configured to move horizontally and independently of the pedestal component, from one end of the pedestal component to an opposite end of the pedestal component and past the pedestal component,
the CT gantry being configured to generate on-line CT scans to guide radiotherapy provided by the medical accelerator, and
the support structure being:
mounted to the base platform or to the pedestal component, in which axial, helical, and/or volumetric CT scans of a patient on the treatment couchtop are obtained via translational motion of the treatment couchtop along an axis passing through the bore of the CT gantry, or
configured to traverse a guided pathway coupled to, or incorporated on, the base platform, in which volumetric CT scans are obtained via:
translational motion of the treatment couchtop along the axis without translational motion of the CT gantry along the axis,
translational motion of the CT gantry via the guided pathway along the axis without translational motion of the treatment couchtop along the axis, or
combined translational motion of the treatment couchtop along the axis and the CT gantry via the guided pathway along the axis.

19. The CT scanner device of claim 18, wherein the support structure is mounted to the base platform and/or to the pedestal component via one or more coupling mechanisms.

20. The CT scanner device of claim 18, wherein the CT scanner device and the treatment couchtop rotate about the beam isocenter of the medical accelerator when the base platform is coupled to, and rotated by, the rotatable floor component.

* * * * *